US012599662B2

(12) United States Patent
Griscelli et al.

(10) Patent No.: US 12,599,662 B2
(45) Date of Patent: Apr. 14, 2026

(54) METHODS AND COMPOSITIONS FOR TREATING CANCERS

(71) Applicants: INSERM (INSTITUT NATIONAL DE LA SANTÉ ET DE LA RECHERCHE MÉDICALE), Paris (FR); UNIVERSITÉ PARIS-SACLAY, Saint-Aubin (FR); ASSISTANCE PUBLIQUE—HÔPITAUX DE PARIS, Paris (FR); UNIVERSITÉDE PARIS, Paris (FR)

(72) Inventors: Frank Griscelli, Villejuif (FR); Ali Turhan, Villejuif (FR); Annelise Bennaceur Griscelli, Villejuif (FR)

(73) Assignees: INSERM (INSTITUT NATIONAL DE LA SANTÉ ET DE LA RECHERCHE MÉDICALE), Paris (FR); UNIVERSITÉ PARIS-SACLAY, Saint-Aubin (FR); ASSISTANCE PUBLIQUE—HÔPITAUX DE PARIS, Paris (FR); UNIVERSITÉ DE PARIS, Paris (FR)

( * ) Notice: Subject to any disclaimer, the term of this patent is extended or adjusted under 35 U.S.C. 154(b) by 1413 days.

(21) Appl. No.: 17/265,580

(22) PCT Filed: Aug. 6, 2019

(86) PCT No.: PCT/EP2019/071112
§ 371 (c)(1),
(2) Date: Feb. 3, 2021

(87) PCT Pub. No.: WO2020/030634
PCT Pub. Date: Feb. 13, 2020

(65) Prior Publication Data
US 2021/0236633 A1 Aug. 5, 2021

(30) Foreign Application Priority Data
Aug. 6, 2018 (EP) .................................... 18306080

(51) Int. Cl.

| | |
|---|---|
| ***A61K 39/39*** | (2006.01) |
| ***A61K 31/167*** | (2006.01) |
| ***A61K 31/19*** | (2006.01) |
| ***A61K 31/4015*** | (2006.01) |
| ***A61K 31/4406*** | (2006.01) |
| ***A61K 39/00*** | (2006.01) |

(Continued)

(52) U.S. Cl.
CPC ............ *A61K 39/39* (2013.01); *A61K 31/167* (2013.01); *A61K 31/19* (2013.01); *A61K 31/4015* (2013.01); *A61K 31/4406* (2013.01); *A61K 40/10* (2025.01); *A61K 40/4202* (2025.01); *A61P 35/00* (2018.01); *A61K 2039/515* (2013.01); *A61K 2039/55561* (2013.01); *A61K 2039/55577* (2013.01); *A61K 2239/31* (2023.05); *A61K 2239/38* (2023.05); *A61K 2239/49* (2023.05)

(58) Field of Classification Search
CPC ................. A61K 39/461; A61K 39/39; A61K 2039/515; A61K 2039/55561; A61K 39/464401; A61K 45/06; A61K 2300/00; A61P 35/00; A61P 35/02; A61P 35/04
See application file for complete search history.

(56) References Cited

U.S. PATENT DOCUMENTS

| | | | |
|---|---|---|---|
| 5,637,483 | A | 6/1997 | Dranoff et al. |
| 2013/0136722 | A1 | 5/2013 | Mahmud |

(Continued)

FOREIGN PATENT DOCUMENTS

| | | | |
|---|---|---|---|
| EP | 2599860 A1 | 6/2013 | |
| WO | 2009/130301 A1 | 10/2009 | |

(Continued)

OTHER PUBLICATIONS

Cui and Qiu (Cancer Immunol Immunother, 2006, vol. 55, pp. 1267-1279) (Year: 2006).*
Tabiasco et at (Jouranal of Immunology, vol. 2006, vol. 177, pp. 8708-8713) (Year: 2006).*
Forghanni and Walker (Breast Cancer Research and Treatment, 2015, vol. 153, pp. 21-30) (Year: 2015).*
Zhao et al (Signal Transduction and Targeted Therapy, 2023, vol. 8, No. 283, 22 pages) (Year: 2023).*
Wang et al, Chem Soc Review, 2013, vol. 42, pp. 4859-4866 (Year: 2013).*
Koorman et al (Cell Stem Cell, Apr. 2018, vol. 22, pp. 501-513 (Year: 2018).*
International Search Report and Written Opinion issued on Nov. 11, 2019 for corresponding PCT Application No. PCT/EP2019/071112.
Conforti, R. et al., “Opposing Effects of Toll-like Receptor (TLR3) Signaling in Tumors Can Be Therapeutically Uncoupled to Optimize the Anticancer Efficacy of TLR3 Ligands,” Cancer Research; vol. 70; No. 2; 2010; pp. 490-500 XP055411323.

(Continued)

*Primary Examiner* — Karen A. Canella
(74) *Attorney, Agent, or Firm* — POLSINELLI PC

(57) ABSTRACT

The invention relates to a method for treating cancers. Many cancers harbour sternness signature to de-differentiate into immature progenitors confer to tumor clones the re-expression of genes from fetal development. Inventors have obtained mice per group which received two boosts of vaccine 7 and 14 days with 2×106 irradiated hESCs cells that were mixed with 3 different adjuvants: 500 µg of TLR3, 50 µg of TLR9 agonist or 50 µg/ml of Quil A® Saponin vaccine adjuvant. After 14 days 5×104 4T1 cells were injected into the mammary fat pad of the mice and Valproic acid added in the drinking water at the dose of 4 mg/ml. They have shown that in contrast to the non-vaccinated mice, the mice vaccinated with hESC combined with a TLR3 agonist have generated the highest reduction of breast tumor volume ($p<0.001$) compared to the use of a TLR9 agonist or to Quil-A® Saponin vaccine adjuvant. Accordingly, the invention relates to a method for treating a subject suffering from a cancer with i) an agent that induces MHC-I presentation of antigens, ii) a vaccine composition containing an immunogenic element and iii) an adjuvant.

16 Claims, 3 Drawing Sheets

Figure 1:
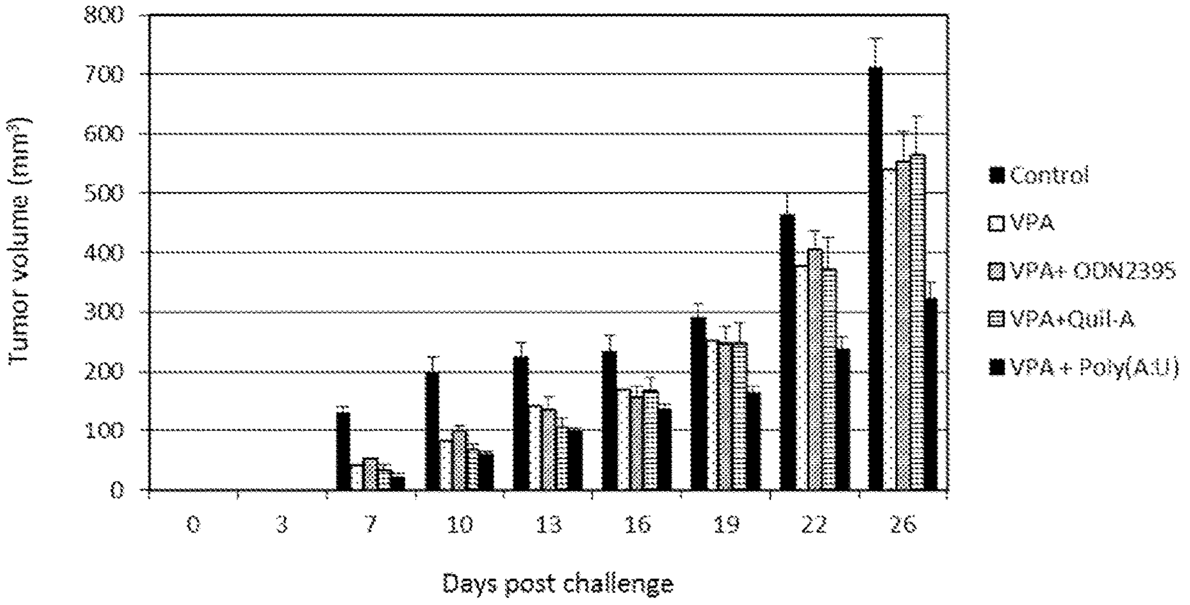

(51) Int. Cl.

*A61K 40/10* (2025.01)
*A61K 40/42* (2025.01)
*A61P 35/00* (2006.01)

(56) References Cited

U.S. PATENT DOCUMENTS

| | | | |
|---|---|---|---|
| 2014/0193458 | A1 | 7/2014 | Bridle et al. |
| 2018/0296850 | A1 | 10/2018 | Wang |

FOREIGN PATENT DOCUMENTS

| | | | |
|---|---|---|---|
| WO | 2012/122629 | A1 | 9/2012 |
| WO | 2016/046651 | A1 | 3/2016 |
| WO | 2016/065330 | A1 | 4/2016 |
| WO | 2017/027757 | A2 | 2/2017 |
| WO | 2017/202949 | A1 | 11/2017 |
| WO | 2019/101956 | A1 | 5/2019 |

OTHER PUBLICATIONS

Bartlett, D. et al., "Oncolytic viruses as therapeutic cancer vaccines," Molecular Cancer, vol. 12, No. 103, 2013, pp. 1-16.

Bear, A.S. et al., "T Cells as Vehicles for Cancer Vaccination," Journal of Biomedicine and Biotechnology, 2011, pp. 1-8.

Bridle, B.W. et al., "HDAC Inhibition Suppresses Primary Immune Responses, Enhances Secondary Immune Responses, and Abrogates Autoimmunity During Tumor Immunotherapy," The American Society of Gene & Cell Therapy, vol. 21, No. 4, 2013, pp. 887-894.

Brodie, S.A. et al., "Could valproic acid be an effective anticancer agent? The evidence so far," HHS Public Access, vol. 14, No. 10, 2014, pp. 1097-1100.

Debeb, B.G. et al., "Histone Deacetylase Inhibitors Stimulate Dedifferentiation of Human Breast Cancer Cells through WNT/ß-catenin Signaling," HHS Public Access, vol. 30, No. 11, 2012, pp. 2366-2377.

Dong, W. et al., "Antitumor Effect of Embryonic Stem Cells in a Non-Small Cell Lung Cancer Model: Antitumor Factors and Immune Responses," International Journal of Medical Sciences, vol. 10. No. 10. 2013, pp. 1314-1320.

Lai, M.D. et al., An HDAC inhibitor enhances the antitumor activity of a CMV promoter-driven DNA vaccine, Cancer Gene Therapy, vol. 17, 2010, pp. 203-211.

Shen, L. et al., "Class I Histone Deacetylase Inhibitor Entinostat Suppresses Regulatory T Cells and Enhances Immunotherapies in Renal and Prostate Cancer Models," PLOS One, vol. 7, Issue 1, 2012; pp. 1-14.

Lindor, N.M. et al., "Concise Handbook of Familial Cancer Susceptibility Syndromes," Second Edition, Journal of the National Cancer Institute Monographs, No. 38, 2008, pp. 1-93.

Lisiero, D.N. et al., "The histone deacetylase inhibitor, LBH589, promotes the systemic cytokine and effector responses of adoptively transferred CD8+ T cells," Journal of ImmunoTherapy of Cancer, vol. 2, No. 8, 2014, pp. 1-12.

Melief, C.J.M. et al., "Therapeutic cancer vaccines," The Journal of Clinical Investigation, vol. 125, No. 9, 2015, pp. 3401-3412.

Rezvani, K. et al., "Cancer Vaccines and T Cell Therapy," Biol. Blood Marrow Transplant, vol. 19, 2013, pp. S97-S101.

Sharkis, S.J. et al., "Pluripotent Stem Cell-Based Cancer Therapy: Promise and Challenges," NIH Public Access, vol. 4, No. 127, 2012, pp. 1-8.

Golla, U. et al., "Investigation of molecular mechanism of action of Valproic acid, an anticancer drug using budding yeast as a model organism," Research Gate, 2015, pp. 1-3.

Vivian, J.L. et al., "An allelic series of mutations in Smad2 and Smad4 identified in a genotype-based screen of N-ethyl-N-nitrosourea-mutagenized mouse embryonic stem cells," PNAS, vol. 99, No. 24, 2002, pp. 15542-15547.

Wu, D. et al., "Effect of targeted ovarian cancer immunotherapy using ovarian cancer stem cell vaccine," Journal of Ovarian Research, vol. 8, No. 68, 2015, pp. 1-10.

Takahashi, K. et al., "Induction of Pluripotent Stem Cells from Mouse Embryonic and Adult Fibroblast Cultures by Defined Factors," Cell, vol. 126, 2006, pp. 663-676.

Yoshizaki, S. et al., "Vaccination with human induced pluripotent stem cells creates an antigen-specific immune response against HIV-1 gp160," Frontiers in Microbiology, vol. 2, Article 27, 2011, pp. 1-8.

Zhang, Y. et al., "Antitumor activity of pluripotent cell-engineered vaccines and their potential to treat lung cancer in relation to different levels of irradiation," OncoTargets and Therapy, vol. 9, 2016, pp. 1425-1436.

Zheng, S. et al., "Retake the Center Stage—New Development of Rat Genetics," Journal of Genetics and Genomics, vol. 39, 2012, pp. 261-268.

Zheng, Q. et al., "A hepatic stem cell vaccine is superior to an embryonic stem cell vaccine in the prophylaxis and treatment of murine hepatocarcinoma," Oncology Reports, vol. 37, 2017, pp. 1716-1724.

* cited by examiner

METHODS AND COMPOSITIONS FOR TREATING CANCERS

CROSS-REFERENCE TO RELATED APPLICATIONS

This application is a national stage application (under 35 U.S.C. § 371) of PCT/EP2019/071112, filed Aug. 6, 2019, which claims benefit of European Application No. 18306080.5, filed Aug. 6, 2018, which are incorporated herein by reference in their entireties.

FIELD OF THE INVENTION

The present invention is in the field of oncology, and more specifically, the invention relates to an anticancer vaccine combined therapy. More particularly, the invention relates to a method for treating a cancer with an agent that induces MHC-I presentation of antigens, (ii) a vaccine composition containing an immunogenic element and iii) an adjuvant.

BACKGROUND OF THE INVENTION

Cancer stem cells (CSCs) represent a minor population of self-renewing cancer cells that are responsive of tumor persistence and recurrence since they are likely to be resistant to conventional treatments. Those CSCs have recently been evidenced in solid tumors from various origins including breast, colon head and neck carcinomas and represent a new therapeutic target. It has shown that those CSC express a large number of embryonic antigens which share the expression with human Embryonic Stem Cells (hESCs) or human Induced Pluripotent Stem Cells (hiPSCs). The expression of some of those embryonic antigens has also been found in differentiated cancer cells that are associated with tumorigenesis and/or tumor progression.

During the last decade, cancer treatment approaches have progressed from targeted therapies to immune intervention strategies with an unprecedented gain on survival as well as cancer related morbidity and mortality. However, despite the proved efficacy and clinical benefits of immune checkpoint inhibitors, there are a large number of partial responders and primary resistance tumors ("innate resistance") caused by immunoregulatory factors affecting tumor-specific immune responses and cancer-cell-autonomous cues. After initial response to PD-1/PD-L1 blockade, acquired resistance occurs in a high number of cancers in progression and relapse. The mechanism underlying acquired resistance to PD1/PDL-1 blockage is caused by evolution of neoantigen landscape with acquired somatic mutations (mutanome), an evolutive tumor immune micro-environment (TIME) with an epigenetic stability of exhausted T cells.

Cancer germline antigens represent proteins that are expressed during embryonic and fetal development and these epigenetically controlled antigens can be re-expressed in a variable proportion of many cancer. To date several human cancer vaccine trials have been set up in order to target embryonic antigens such as carcinoembryonic antigen (CEA), alpha fetoprotein or cancer/testes antigens (NY-ESO-1). Adoptive cell transfer with autologous lymphocytes genetically engineered to express a T cell antigen receptor (TCR) for the HLA-A-0201 epitope of cancer germline antigen NY-ESO-1, led to durable tumor regression in some patients with metastatic melanoma. Unfortunately, targeting one antigen alone was shown to be not efficient enough to generate strong antitumor immune responses to mediate tumor rejection because of rapid appearance of escape mutants and novel somatic neo-antigens and the general inefficiency of monovalent cancer vaccines.

Recent interest in the potential of stem cells in regenerative medicine has made well-defined undifferentiated ESC lines widely available as well as undifferentiated iPSCs that are phenotypically and functionally similar to ESCs.

Cancer harboring stemness signature present a genomic plasticity with a profound change of the chromatin landscapes secondary to intrinsic pathways and inducing factors from a strong immunosuppressive tumor micro-environment. Their ability to de-differentiate into immature progenitors confer to tumor clones the re-expression of genes from fetal development with a down-regulation of MHC Class I and up-regulation of co-inhibiting molecules expression.

Thus, there continues to be a need for new approaches to prevent and/or treat cancers having stem cells signature. Vaccination against stem cell mutant neo-epitopes could be used to potentiate the immune response of adoptively transferred T cells or cells activated through immunological checkpoint blockade.

This and other needs are addressed in whole or in part by the presently disclosed subject matter.

SUMMARY OF THE INVENTION

The present invention relates a method for treating a subject suffering from a cancer, comprising a step of administering simultaneously, separately or sequentially to said subject a therapeutically amount of (i) an agent that induces MHC-I presentation of antigens, (ii) a vaccine composition containing an immunogenic element and iii) an adjuvant. The present invention is defined in particular by the claims. In particular, the agent that induces MHC-I presentation of antigens is a histone deacetylase inhibitor (HDACi) and the adjuvant is an agonist of toll-like receptor (TLR) 3. It is preferred when the subject has not pre-existing immunity against the antigen.

In a particular embodiment, the immunogenic element in the vaccine composition is selected from the group consisting of:

a. an antigen of interest,
b. human Embryonic Stem Cells (hESCs) composition,
c. human Induced Pluripotent Stem Cells (hiPSCs) composition,
d. fetal stem cell composition,
e. an extract from a cell composition, wherein cells of said composition express an antigen of interest,
f. a cell composition, wherein cells of said composition express an antigen of interest,
g. a cell composition comprising Antigen-Presenting-Cells that have been primed in vitro by antigens of interest, and
h. T cell lymphocytes that have been primed in vitro against the antigen of interest by exposure to Antigen-Presenting-Cells presenting the antigen of interest.

In particular, the antigen is a fetal antigen or a multiplicity of fetal antigens.

In an embodiment, the vaccine composition comprises cells of the population express one or more antigen(s) of interest also expressed by the cancer cells of the subject.

In an embodiment, the vaccine composition comprises a population of inactivated fetal cells expressing neo-fetal antigens.

In particular, the fetal stem cells have been obtained by a process comprising the steps of a. Differentiation of a population of pluripotent cells towards the pathway pertaining to the specific cancer of the patient b. Expansion of the cells thus differentiated c. Optionally exposition of to a mutagenic agent during expansion, to induce mutagenesis of genes in cells of said population d. Verification that at least 70% of the cells of the population express fetal markers e. Optionally verification that the cells of the population express at least one tumor associated antigen (TAA) or neo-antigen that is present in the subject's cancer cells, f. Inactivation of the cells, in order for the cells to lose their ability to divide.

In an embodiment, the vaccine composition comprises a population of inactivated pluripotent cells such as Embryonic Stem Cells (hESCs) or Induced Pluripotent Stem Cells (hiPSCs) expressing neo-fetal antigens. Such populations are disclosed in WO2017202949.

In particular, the pluripotent cells have been obtained by a process comprising the steps of a. expanding pluripotent cells, in the presence of such conditions as to maintain the pluripotent ability of the cells, optionally in the presence of an agent that induces MHC-I presentation of antigens in said population during the expansion step b. and exposing the expanded cells to an inactivating agent that will inactivate the cells, while maintaining the cell envelope integrity.

It is preferred when the histone deacetylase inhibitor is selected from the group consisting of Valproic acid (VPA), Vorinostat, Panobinostat, Givinostat, Belinostat, Entinostat, Mocetinostat, Practinostat, Chidamide, Quisinostat, Abexinostat, and Levetiracetam.

It is preferred when the TLR3 agonist is Poly(A:U) or poly(I:C).

In an embodiment, an initial administration of the vaccine composition containing an immunogenic element and the agonist of TLR 3 is performed and multiple administrations of the histone deacetylase inhibitor are performed from said initial administration.

In an embodiment, the cancer is selected from the group consisting of bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, renal carcinoma, head and neck tumor, and all sub-type of solid tumor, hematopoietic malignancies and RET-mutated endocrine tumors including medullary thyroid cancer.

In an embodiment, the cancer is a hormone-dependent cancer. In this embodiment, the cancer is selected from a breast cancer, a prostate cancer, a uterus cancer and an ovary cancer.

The invention relates to a combined preparation of (i) a histone deacetylase inhibitor (HDACi) (ii) a vaccine composition containing an immunogenic element and iii) an agonist of toll-like receptor (TLR) 3 for use by simultaneous, separate or sequential administration for treating a cancer in a subject.

In an embodiment, the immunogenic element in the vaccine composition is selected from the same group as above, in particular a fetal antigen or a multiplicity of fetal antigens, cells of the population express one or more antigen(s) of interest also expressed by the cancer cells of the subject, a population of inactivated fetal cells expressing neo-fetal antigens or a population of inactivated pluripotent cells, such as Embryonic Stem Cells (hESCs) or Induced Pluripotent Stem Cells (hiPSCs) expressing neo-fetal antigens.

DETAILED DESCRIPTION OF THE INVENTION

Inventors have obtained five mice per group which received two boosts of vaccine 7 and 14 days with 2×106 irradiated hESCs cells that were mixed with 3 different adjuvants: 500 µg of TLR3, 50 g of TLR9 agonist or 50 g/ml of Quil-A® Saponin vaccine adjuvant. After 14 days 5×104 4T1 cells were injected into the mammary fat pad of the mice and Valproic acid added in the drinking water at the dose of 4 mg/ml. They have shown that in contrast to the non-vaccinated mice, the mice vaccinated with hESC combined with a TLR3 agonist have generated the highest reduction of breast tumor volume ($p<0.001$) compared to the use of a TLR9 agonist or to Quil-A® Saponin vaccine adjuvant.

Method for Treating a Subject Suffering from a Cancer

Accordingly, the invention relates to a method for treating a subject suffering from a cancer, comprising the step of administering simultaneously, separately or sequentially to said subject a therapeutically amount of (i) an agent that induces MHC-I presentation of antigens, ii) a vaccine composition containing an immunogenic element and iii) an adjuvant, as a combined preparation.

As used herein, the terms "treating" or "treatment" refer to both prophylactic or preventive treatment as well as curative or disease modifying treatment, including treatment of subject at high predisposed risk of contracting cancer such as hereditary family cancer syndromes or suspected to have contracted a cancer as well as subject who are ill or have been diagnosed as suffering from a cancer or medical condition, and includes suppression of clinical relapse. The treatment may be administered to a subject having a cancer or who ultimately may acquire the cancer, in order to prevent, cure, delay the onset of, reduce the severity of, or ameliorate one or more symptoms of cancer or recurring cancer, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, (e.g., weekly, monthly, yearly, etc.) or intermittent therapy (e.g., interrupted treatment, intermittent treatment, treatment at relapse, or treatment upon achievement of a particular predetermined criteria (e.g., pain, disease manifestation, etc.).

As used herein, the term "cancer" refers to an abnormal cell growth with the potential to invade or spread to other parts of the body. The cancer is selected from the group consisting of, but not limited to bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, renal carcinoma, head and neck tumor, and all sub-type of solid tumor, hematopoietic malignancies and RET-mutated endocrine tumors including medullary thyroid cancer.

As used herein, the term "subject" refers to any mammals, such as a rodent, a feline, a canine, and a non-human and human primate. Particularly, in the present invention, the subject is a human afflicted with or susceptible to be afflicted with cancers which having an expression of pluripotent embryonic-like stem cell antigens or fetal-like stem cell antigens. Typically, the subject is a human afflicted with or susceptible to be afflicted with cancers as described above.

As used herein, the term "agent that induces MHC-I presentation of antigens" refers to a compound which is capable of stimulating immunogenicity. Such compound is called activator of MHC expression and/or immune response in a subject. Inducement of MHC-I can be assessed by determining an increase of at least 2-fold of the MHC-I molecules at the surface of cancer cells (such as 4T1 cells, or lewis lung carcinoma, LLC cells), by flow cytometry analysis (FACS). The term "MHC" refers to major histocompatibility complex which is present on the cell surface to recognize foreign molecules, called antigens. MHC binds to antigens and presents them to immune molecules such as lymphocytes T and B. The term "immune response" refers to immunological response of immune system to an antigen. By activating the immune response, the population of FoxP3 subpopulation and myeloid-derived suppressor cell (MDSC) are decreased and, in contrary the NK population is increased. In the context of the invention, the immune response against tumors comprises a cytotoxic T cell response against an antigen present in or on a cell of the tumor. In some embodiments, the cytotoxic T cell response is mediated by CD8+ T cells. Typically, in the context of the invention, the antigen which activates the MHC expression and/or immune response corresponds to the molecules present on the population of fetal stem cells as described above. In this case, the compound which activates the MCH expression and/or immune system is a fetal gene or an immunogenic neo-antigen. The term "neo-antigen" or "neo-antigenic" means a class of antigens that arises from at least one mutation which alters the amino acid sequence of genome encoded proteins.

In the context of the invention, compounds are selected from the group consisting of: cytokines, histone deacetylase (HDAC) inhibitors, DNA methyltransferase inhibitors, and histone-lysine N-methyltransferase enzyme inhibitors.

In a particular embodiment, the activator of MHC expression and/or of immune response is a histone deacetylase inhibitor. HDAC inhibitors (HDACi) are natural or synthetic chemical compounds that have broad functions in the cell. Various HDACi are known and were designed to target the catalytic sites of HDACs. According to their structure and specificity, HDACi can be grouped into several classes, including hydroxamates, cyclic peptides, aliphatic acids, and benzamides. A compound can be tested for HDACi activity by methods as disclosed in Blackwell et al (Life Sciences 82 (2008) 1050-1058) or Kozikowski et al (Journal of Medicinal Chemistry 50 (13), 3054-3061).

As used herein, the term histone "histone deacetylase inhibitor" called also HDACi, refers to a class of compounds that interfere with the function of histone deacetylase. Histone deacetylases (HDACs) play important roles in transcriptional regulation and pathogenesis of cancer. Typically, inhibitors of HDACs modulate transcription and induce cell growth arrest, differentiation and apoptosis. HDACis also enhance the cytotoxic effects of therapeutic agents used in cancer treatment, including radiation and chemotherapeutic drugs.

In a particular embodiment, the histone deacetylase inhibitor is valproic acid (VPA).

The term "valproic acid" refers to acid-2-propylpentanoic ($C_8H_{16}O_2$), which has the following CAS number and formula 99-66-1 in the art:

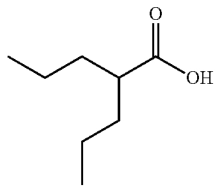

The biological activities of valproic acid are multiple (Chateauvieux et al, J. Biomed. Biotechnol, 2010, pii: 479364. doi: 10.1155/2010/479364). Valproic acid affects the neurotransmitter GABA (Gamma Amino Butyrate) potentiating inhibitory activity. Several mechanisms of action are suggested. Valproic acid is particularly the GABA metabolism: inhibits degradation of GABA, GABA Transaminobutyratre (LAMP), acroissement of GABA synthesis, and modifies its turnover. In addition, valproic acid blocks certain ion channels, reduces arousal mediated by the N-Methyl-D-Aspartate, and blocks the activity of ion channels including Na+ and Ca 2+ (voltage-dependent L-type CACNA1 type C, D, N, and F).

In the context of the invention, valproic acid is used as an immune-stimulant to boost immune response against cancers expressing cancer human embryonic stem cells, pluripotent cells are exposed to a mutagenic agent or fetal stem cell neo-antigens shared with fetal stem cells.

More particularly, VPA is used to stimulate and enhance the expression of MHC-I on cancer stem cell compartment, increasing the neo-antigen content in some tumor cells. Higher expression of MHC I on fetal stem cells allow to enhance the presentation of neo-antigens associated with MHC-I to APC/Dendritic cells to induce TH1 immune response. Higher level of chemokines (CXCL9, CXCL10) allow to enhance the recruitment of T cell into the tumor.

The present invention relates to methods to increase the neo-antigen content in derived human embryonic stem cells, pluripotent cells which are exposed to a mutagenic agent or fetal stem cells in the presence of an HADCi such as VPA and/or 5 Azacytidine and in the tumor cells with expression of fetal antigens through chromatin remodelling, as well as chemokines expression (CXCL9, CXCL10, CXL13).

In particular, when used for treating a subject in vivo, the present compositions and vaccines makes it possible to modify the tumor microenvironment and promote the recruitment of T cells into the tumor, so as to obtain a long term durable reduction of tumor volume.

This is due to a synergistic effect of human embryonic stem cells, pluripotent cells which are exposed to a mutagenic agent or fetal stem cell vaccine and VPA co-administration, that is further improved when the HDACi is further administered to the patient, for a period of time (such as at least 15 days) after vaccine injection.

In a particular embodiment, the histone deacetylase inhibitor is suberoylanilide hydroxamic acid, also called Vorinostat (N-Hydroxy-N'-phenyloctanediamide) was the first histone deacetylase inhibitor approved by the U.S. Food and Drug Administration (FDA) on 2006 (Marchion D C et al 2004; Valente et al 2014).

In a particular embodiment, the histone deacetylase inhibitor is Panobinostat (LBH-589) has received the FDA approval on 2015 and has the structure as described in Valente et al 2014.

In a particular embodiment, the histone deacetylase inhibitor is Givinostat (ITF2357) has been granted as an orphan drug in the European Union (Leoni et al 2005; Valente et al 2014).

In another embodiment, the histone deacetylase inhibitor is levetiracetam: although this compound has no direct effect on HDACs, its major carboxylic acid metabolite in humans, 2-pyrrolidinone-n-butyric acid (PBA), inhibited HDACs with Ki values of 2.25+/−0.78 mM (Eyal S, Epilepsia. 2004 July; 45(7):737-44). It is thus considered to be a HDACin in the present context.

In a particular embodiment, the histone deacetylase inhibitor is Belinostat also called Beleodaq (PXD-101) has received the FDA approval on 2014 (Ja et al 2003; Valente et al 2014).

In a particular embodiment, the histone deacetylase inhibitor is Entinostat (as SNDX-275 or MS-275). This molecule has the following chemical formula ($C_{21}H_{20}N_4O_3$) and has structure as described in Valente et al 2014.

In a particular embodiment, the histone deacetylase inhibitor is Mocetinostat (MGCD01030) having the following chemical formula ($C_{23}H_{20}N_6O$) (Valente et al 2014).

In a particular embodiment, the histone deacetylase inhibitor is Practinostat (SB939) having the following chemical formula ($C_{20}H_{30}N_4O_2$) and the structure as described in Diermayr et al 2012.

In a particular embodiment, the histone deacetylase inhibitor is Chidamide (CS055/HBI-8000) having the following chemical formula ($C_{22}H_{19}FN_4O_2$).

In a particular embodiment, the histone deacetylase inhibitor is Quisinostat (JNJ-26481585) having the following chemical formula ($C_{21}H_{26}N_6O_2$).

In a particular embodiment, the histone deacetylase inhibitor is Abexinostat (PCI24781) having the following chemical formula ($C_{21}H_{23}N_3O_5$) (Valente et al 2014).

In a particular embodiment, the histone deacetylase inhibitor is CHR-3996 having the following chemical formula ($C_{20}H_{19}FN_6O_2$) (Moffat D et al 2010; Banerji et al 2012).

In a particular embodiment, the histone deacetylase inhibitor is AR-42 having the following chemical formula ($C_{18}H_{20}N_2O_3$) (Lin et al 2012).

In a particular embodiment, the activator of MHC expression is DNA methyltransferase inhibitors.

As used herein, the term "DNA methyltransferase inhibitors" refer to compounds which are capable of interacting with DNA methyltransferase (DNMT) and inhibiting their activity. DNMT are the enzymes which catalyze the transfer of a methyl group to DNA. DNA methylation serves a wide variety of biological functions. All the known DNA methyltransferases use S-adenosyl methionine (SAM) as the methyl donor.

In a particular embodiment, the DNA methyltransferase inhibitor is azacytidine, also known as 5-aza-2-deoxycytidine having the following chemical formula ($C_8H_{12}N_4O_5$) and structure in the art (Kaminskas et al 2004; Estey et al 2013).

In a particular embodiment, the DNA methyltransferase inhibitor is decitabine also known as 5-aza-2'-deoxycytidine, having the following formula ($C_8H_{12}N_4O_4$) (Kantarjian et al 2006).

In a particular embodiment, the activator of MHC expression and/or immune response is a histone-lysine N-methyltransferase enzyme inhibitor, or DNA methyltransferase inhibitor. As used herein, the term "histone-lysine N-methyltransferase enzyme inhibitor" refers to compounds which are capable of interacting with histone-lysine N-methyltransferase enzyme encoded by Enhancer of zeste homolog 1 (EZH1) and 2 (EZH2) gene that participates in DNA methylation. EZH2 catalyzes the addition of methyl groups to histone H3 at lysine 27 by using the cofactor S-adenosyl-L-methionine.

In a particular embodiment, the histone-lysine N-methyltransferase enzyme inhibitor is 3-Deazaneplanocin A (DZNep, C-c3Ado). DZNep, C-c3Ado has the following chemical formula $C_{12}H_{14}N_4O_3$ and CAS number 102052-95-9 in the art.

In a particular embodiment, the histone-lysine N-methyltransferase enzyme inhibitor is UNC1999 and an inactive analog compound. UNC1999 has the following chemical formula $C_{33}H_{43}N_7O_2$ and CAS number 1431612-23-5 in the art.

In a particular embodiment, the histone-lysine N-methyltransferase enzyme inhibitor is UNC2400 and an inactive analog compound. UNC2400 has the following chemical formula $C_{35}H_{47}N_7O_2$ and CAS number 1433200-49-7 in the art.

In a particular embodiment, the histone-lysine N-methyltransferase enzyme inhibitor is tazemetostat (EPZ6438, E7438). Tazemetostat has the following chemical formula $C_{34}H_{44}N_4O_4$ and CAS number 1403254-99-8 in the art.

In a particular embodiment, the histone-lysine N-methyltransferase enzyme inhibitor is trifluoroacetate (EPZ011989). Trifluoroacetate has the following chemical formula $CF_3COONa$ and CAS number 2923-18-4 in the art.

In a particular embodiment, the histone-lysine N-methyltransferase enzyme inhibitor is EPZ005687. EPZ005687 has the following chemical formula $C_{32}H_{37}N_5O_3$ and CAS number 1396772-26-1 in the art.

In a particular embodiment, histone-lysine N-methyltransferase enzyme inhibitor is GSK343. GSK343 has the following chemical formula $C_{31}H_{39}N_7O_2$ and CAS number 1346704-33-3 in the art.

In a particular embodiment, histone-lysine N-methyltransferase enzyme inhibitor is GSK126. GSK126 has the following chemical formula $C_{31}H_{38}N_6O_2$ and CAS number 1346574-57-9 in the art.

In a particular embodiment, histone-lysine N-methyltransferase enzyme inhibitor is GSK2816126. GSK2816126 has the following chemical formula $C_{31}H_{38}N_6O_2$ and CAS number 1346574-57-9 in the art.

In a particular embodiment, histone-lysine N-methyltransferase enzyme inhibitor is ZLD1039. ZLD1039 has the following chemical formula $C_{36}H_{48}N_6O_3$ and CAS number 1826865-46-6 in the art.

As used herein, the term "a vaccine composition" refers to vaccine composition containing an immunogenic element intended to make the subject develop an immune response against one or more antigen(s) of interest. An antigen of interest is any antigen against which an immune response is desired, and include any peptide, protein either from the self (such as antigens from cancer cells) or exogenous such as bacterial, viral, or parasitic protein, other kind of antigens such as nucleic acids, sugars, lipopolysaccharides and the like.

In a particular embodiment, the vaccine composition contains an immunogenic element (compound) intended to make the subject develop an immune response against one or more antigen(s) of interest.

In another embodiment, the immunogenic compound is an extract from a cell composition, wherein cells of said composition express an antigen of interest. The cellular extract may be lysed cells that have been centrifuged to remove insoluble matter such as membrane fragments, vesicles, and nuclei, and thus consist mostly of cytosol. In another embodiment, the extract may have been made using specific techniques to deplete or enrich specific components (for example sonication can be used to break large membrane fragments into small particles that remain in the extract, or high speed centrifugation to remove the smallest insoluble components). The cell extract is obtained by any chemical or mechanical action, such as by pressure, distillation, evaporation and the like.

As used herein, the term the "immunogenic element" refers to compounds which stimulate the immune system. In the context of the invention, the immunogenic element is selected from the group consisting of but not limited to:

a) an antigen of interest,
b) human Embryonic Stem Cells (hESCs) composition,
c) human Induced Pluripotent Stem Cells (hiPSCs) composition,
d) fetal stem cell composition,
e) an extract from a cell composition, wherein cells of said composition express an antigen of interest,
f) a cell composition, wherein cells of said composition express an antigen of interest,
g) a cell composition comprising Antigen-Presenting-Cells that have been primed in vitro by antigens of interest, or
h) T cell lymphocytes that have been primed in vitro against the antigen of interest by exposure to Antigen-Presenting-Cells presenting the antigen of interest.

Methods for Obtaining Cell Composition:

In another embodiment, the immunogenic element is a cell composition, wherein cells of said composition express the antigen of interest.

In a particular embodiment, the cell composition is human Embryonic Stem Cells (hESCs) composition, human Induced Pluripotent Stem Cells (hiPSCs) composition or fetal stem cell composition.

Population and Use of Fetal Cells

In the present context, a population of fetal cell corresponds to a population of cells that are maintained as a cell culture, but also encompass organoids, where the cells are starting to create an organ and where a 3D spatial organization of the cells can be observed.

It is reminded that differentiation is the process by which a more specialized cell is formed from a less specialized cell. It is a continuous process. Starting from a pluripotent cell (embryonic stem cells, or iPS cells), the cells will lose the pluripotency, and engage into one way of differentiation, where it will mature in a fully differentiated specialized cell. For some organs, multiple cells will create organoids, during the differentiation process.

Inducing and directing the differentiation of pluripotent cells is known to the person of skill in the art. One can cite Wu et al (Cell. 2016 Jun. 16; 165(7):1572-1585), Fatehullah et al (Nat Cell Biol. 2016 March; 18(3):246-54) or Sasaki and Clevers (Curr Opin Genet Dev. 2018 Sep. 24; 52:117-122) that describe development or organoids from pluripotent cells. There are multiple other articles that describe the said population and teach methods and conditions to have pluripotent cells differentiate in various tissues of interest.

In an embodiment, the immunogenic element is a population of fetal cells that have been inactivated, the fetal cells advantageously being in the same cellular differentiation lineage than the cancer to be treated.

In this embodiment, the invention relates to a combination of (i) a histone deacetylase inhibitor (HDACi) and (ii) a vaccine composition containing a population of inactivated fetal cells, and iii) an adjuvant, wherein the adjuvant is an agonist of toll-like receptor (TLR) 3, for use in the treatment of a cancer in a subject.

In another embodiment, the vaccine consists of a population of inactivated fetal cells. In particular, cells of the population express one or more antigen(s) of interest also expressed by the cancer cells of the subject. In a specific embodiment, the population of inactivated fetal cells is an organoid or is derived from an organoid (i.e. has been obtained by disrupting the 3D structure of the organoid).

Generally speaking, the term "fetal stem cell" refers to a population of fetal cells which are transient progenitors appearing during the early stage of development. This kind of population can be reproduced in vitro by differentiation of allogeneic, xenogeneic or syngeneic pluripotent stem cells (ESC and iPSC). Fetal population cells are characterized by the loss of genes related to pluripotency with at least 20% of loss of the following genes NACC1, BLM, WDR33, DAZAP1, CDK1, CDC45, ZNF165, XRCC5, SMARCAD1, AIMP2, CKS1B, NANOG, ZFP42, U2AF1, CCNB2, DCTPP1, TGIF1, SUPT3H, AURKB, GEMIN7, SRSF1, PNP, SIGLEC12, POU5F1, PSMA3, RMND5B, GDF9, STXBP2, BAG6, GMPS, PCNA, NME1, POP7, RCHY1, SMARCC1, HNRNPK, PTMA, NPM1, SNRPA, MYBBP1A, CDT1, HSPD1, TRIM28, PHF10, GRB7, HSPE1, DAXX, FAM136A, KPNA2, FUS, PNN, RFC3, HPRT1, PA2G4, SNRPE, RBPMS, PRMT5, PIAS2, BYSL, POLD2, LSM5, TDGF1, NOP56, EPPK1, TARBP2, MRE11A, CDC7, SRSF3, TNNI3, NUDT1, DIAPH1, PPID, CDA, GADD45A, MCM6, SNURF, CDC25C, TNFRSF8, STIP1, ACTA1, POLR1D, TUBA3C, RPA1, VAMP8, UNC119, COIL, BIK, PARP1, SP1, CHEK2, NLE1, RPA2, HDAC1, KPNB1, LSM7, TMSB4Y, HMGA1, POLR1C, LSM1, EXO1, MCM5, ITGB3BP, LSM6, UNG, PSMA6, CCNE1, SMNDC1, SET, FKBP3, TK1, CTBP2, POLQ, PLSCR1, GMNN, RND1, NUP153, PHGDH, SNRPB, HSPA14, HSPH1, TCOF1, ANP32A, PELP1, MBD2, HIST1H2BC, TMPO, SPAG5, DNMT3B, LCK, ARMC6, COPS6, MCM3, PPAP2C, LSM4, NME1-NME2, EWSR1, POLG2, BCL2, NFKBIB, SALL4, PXN, EXOSC8, HSPA2, HMGB1, RUVBL1, GOT2, PPM1B, ATIC, DHCR24, APEX1, RFC2, WDYHV1, NTHL1, EXOSC7, SNRPD1, DPPA2, MRPS12, FBL, POLD1, MCM10, EXOSC3, NOP58, TPX2, PAK3, HNRNPAB, ANXA2, BUB1B, SEPHS1, WDR77, LUC7L3, VASP, MCM4, PAK1, PMAIP1, PBX1, NOLC1, PCYT1B, NCL, ORC6, GPRIN2, ORC1, RAD51, HSPA8, ANXA3, NUP50, SNRPC, HAUS1, MATK, BIRC5, MYC, GEMIN6, PSIP1, DSCC1, STRBP, SMN1, EXOSC9, TOE1, GEMIN2, TRIP13, ORC2, MSH3, MNAT1, KIT, RFC5, FOXO4, AATF, RBM14, ZNF281, NPPB, RPA3, APOE, PFDN6, COPS3, CCND1, CXADR, MCM2, ANAPC1, SUMO1, SSB, HSP90AB1, TRAIP, PHC1, LRIF1, LSM3, SNRPN, RPP40, MSH2, FBP1, PFN1, OTX2, STX3, STXBP3, GTF2H2, ELAC2, TCERG1, ERCC5, PASK, ZNF593, PSME3, WRN, ARID3B, ERBB3, POP1, KAT7, PTPN6, SYNCRIP, SIRT1, SLC19A1, ARL4A, CEBPZ, MSH6, AURKA, BAK1, MTHFD1, HSPA9, MYBL2, POP5, RFC4, CHEK1, BCCIP, SOCS1, PHB, PMF1, MPP6, NOC2L, HDAC2, CENPE, RECQL4, CASP6, GNL3, SRSF2, BRIX1, MYB, RNMTL1, DHFR, FEN1, SNRPF, MUTYH, PRNP, MT1G, PSMD11, GARI, DDX11, FUBP1, CDK7, WRAP73, CASP9, RASL11B, CHAF1A, CCNB1, CKS2, CCNA2, PPAN, WEE1, TP53, HMMR, TDP2, RAD9A or RAD54L. In particular, the fetal stem cells are also characterized by the absence of expression of lineage specific genes of adult differentiated cells.

More specifically, it is preferred when the fetal stem cells have been obtained by a process comprising the steps of a. Differentiation of a population of pluripotent cells towards the pathway pertaining to the specific cancer of the patient
b. Expansion of the cells thus differentiated
c. Optionally exposition of to a mutagenic agent during expansion, to induce mutagenesis of genes in cells of said population
d. Verification that at least 70% of the cells of the population express fetal markers
e. Optionally verification that the cells of the population express at least one tumor associated antigen (TAA) or neo-antigen that is present in the subject's cancer cells,
f. Inactivation of the cells, in order for the cells to lose their ability to divide.

When mutagenesis is performed, it is preferred when the mutagenic agent is selected from the group consisting of chemical mutagenic agents and radiation mutagenic agent (X-Ray, UV radiation). In particular, the mutagenic agent is selected from the group consisting of ENU, reactive oxygen species, deaminating agents, polycyclic aromatic hydrocarbons, aromatic amines and sodium azide.

In preferred embodiments, the histone deacetylase inhibitor is selected from the group consisting of Valproic acid (VPA), Vorinostat, Levetiracetam, Panobinostat, Givinostat, Belinostat, Entinostat, Mocetinostat, Practinostat, Chidamide, Quisinostat and Abexinostat. Valproic acid (VPA), Vorinostat and Levetiracetam are of particularly interest.

It is preferred when the composition of inactivated cells comprising inactivated fetal stem cells has been obtained from iPS-derived fetal hematopoietic lineage, and when cells in said population present a mutation rate of at least 0.1% after expansion, in at least one gene selected from the group consisting of: ARHGEF10L, TRIM66, NKAIN, ITGAGGT1, PDZD, MUC4, MUC2, NECAB3, MNT, GLTSCR1, COPZ2, ZFP36, MIB2, ABCC12, IGFN1, LRRK2, RIN3, GGT1, ANK2, HDAC7, MUC20, SDCCAG3, DNAI1, BTNL9, ABTB2, MC2R, DOCK4, FSD1L, CRP, PPP1R3A, SLC22A17, PITPNM1, A2M, CTDSP2, IFNA14, KIF5C, THNSL2, GTF3C3, NRXN1, MED26, FNBP1, TMCO3, ING1, ZNF292, RBL1, CD109, FOXRED2, PLIN2, ZNF85, SESN1, CENPE, BTBD7, STOM, ZNF317, TET1, LRBA, MED4, CDC27, BCR, HPRT1, NASP, and MSH2. These genes are commonly expressed in acute leukemia, in particular in acute myeloid leukemia.

In one embodiment, the composition of inactivated fetal cells comprises inactivated fetal stem cells in iPS-derived renal organoid, wherein cells in said population express at least one fetal antigen selected from the following group: TRAPPC4, MX1, ITSN1, DNAJC7, TAF15, TMEM88, CRYM, PRTG, TYRO3 C12ORF60, FJX1, ADM, FAM45A, ASS1, CA2, ZFHX4, CLVS1, NRG1, EZH2, SLC22A23, MSH5, FBN2, GTF2H2, LIX1, HESX1, FZD5, LRP2, RHOQ, NUAK2, ILF2, ACP6, RPL5, NMNAT1, IDI, U2AF2, KLHL14, CDH2, GREB1L, ARRDC4, THBS1, BMP4, LRIG3, SOX5, SF1, LGR4, MGEA5, BCORL1, STOM, GLIS3, ANXA1, KDM4C, SDC2, TMEM130, MAGI2, GLI3, HEY2, TPBG, ID4, MYLIP, ENC1, EGR1, CDH6, NPY1R, SEL1L3, LRAT, CLDN1, CEP97, BHLHE40, ARL5A, ARL4C, ZNF385B, LYPD1, B3GNT7, INSIG2, ARHGAP29, NOTCH2, and IFI16. These genes are commonly expressed in primary adult renal carcinoma associated or not with c-Met mutation.

In one embodiment, the composition of inactivated fetal cells comprises inactivated fetal stem cells in iPS-derived lung organoid, wherein cells in said population express at least one fetal antigen selected from the following group: AIM2, AQP4, AURKA, BMP5, CDCA7, CEP55, CYP4B1, DACH1, EMP2, EPB41L4A, GJB2, MAOA, MELK, MKI67, NEBL, NFIA, PHF19, RNF144B, and UHRF1. These genes are commonly expressed in adult lung carcinoma.

The invention also relates to a vaccine composition comprising:

a. a population of inactivated fetal stem cells
b. an agent that stimulates immune response and/or MHC I expression, and
c. an adjuvant that is an agonist of toll-like receptor 3, in particular a poly I:C or poly A:U.

In particular, the inactivated fetal stem cells contain mutagenized fetal stem cells. It can be used for treatment of a cancer in a subject, especially when the cancer has fetal stem cells signature.

Also part of the invention is a kit comprising a vaccine composition as disclosed above and an information leaflet providing instructions for immunization.

The invention also relates to a combined preparation of i) a population of inactivated fetal stem cells, ii) a compound which activates MHC expression and/or immune response and iii) an agonist of toll-like receptor 3, for use by simultaneous, separate or sequential administration for treating a cancer in a subject. This can be used when the cancer is selected from the group consisting of bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, renal carcinoma, head and neck tumor, and all sub-type of solid tumor and hematopoietic malignancies.

Methods of treatment wherein a therapeutic amount of the composition (inactivated fetal cell population and adjuvant) is administered to the patient in need thereof are also disclosed and part of the invention.

In the present application, all genes are indicated with their names as known by the person skilled in the art. From such names, one can find the sequence of the genes and proteins, by using any search engine (including generalist search engines) or in databases specific for maintaining libraries of cancer genes, such as the COSMIC database (Catalogue Of Somatic Mutations In Cancer, developed by the Sanger Institute in the UK) or the Cancer Genome Atlas (TCGA, maintained by the NCBI in the US). These databases regroup various sequences coding for antigens expressed in cancer cells.

A fetal cell is thus a cell that has lost its pluripotency as it has started to engage in a differentiation pathway (endoderm, mesoderm, ectoderm).

It is possible to determine whether a population of cells is a population of fetal cells as the cells shall express fetal markers (see below) and not express pluripotency markers.

A population, according to the present invention, contains a large number of cells (at least $0.5\times10^6$ cells, more preferably at least $1\times10^6$ cells, more preferably at least $2\times10^6$ cells or $5\times10^6$ cells or more than $5\times10^6$.

In order to determine whether a population of cells is a population of fetal cells, one must (a) Determine that the cells of the population essentially don't express pluripotency genes (or markers)

(b) Determine the presence of fetal genes (or markers) expressed by cells of the population In a specific embodiment, the cells of the fetal cell population are such that there is (a) no cells or less than 10% of cells express genes typically expressed in undifferentiated pluripotent self-renewing cells (Embryonic Stem cells or induced Pluripotent Stem cells). this is preferably determined by flow cytometry and more specifically by FACS (Fluorescence-activated cell sorting) and (b) at least 70%, more preferably more than 75%, more preferably more than 80% of cells in the population express progenitor/fetal markers, regardless of whether the population is in the form of committed differentiated progenitors derived from three germline layers or of 3D-organoid tissues It is also preferred when less than 10% of cells express adult tissue markers. The adult tissue markers are markers (proteins or genes) that are expressed in adult cells.

The percentages mentioned above relate to the percentage of cells in the population that express the given markers. As an illustration, low expression (<10%) of master genes typically expressed in undifferentiated pluripotent self-renewing cells indicates that less than 10% of the cells of the population express the genes that are looked at, as further explained below.

It is reminded that the markers that are expressed vary during the differentiation process. Consequently, some markers associated with the fetal nature of the cells are expressed early in the differentiation process (i.e. quickly after loss of the pluripotency) whereas some markers are expressed late in the process (i.e. before the maturation in adult cells). Lack of expression of these fetal markers indicates that the cells have lost their fetal characteristics, and likely acquired a phenotype indicating that they have matured into differentiated adult cells.

In order to determine that (a) pluripotency genes aren't express by the cells of the population, it is possible to use gene expression and/or immunocytochemistry evaluation.

The aim is to show absence or low expression of master genes typically expressed in undifferentiated pluripotent self-renewing cells (embryonic stem cells and Induced Pluripotent Stem cells).

In particular, one can a) Use a population of iPS cells as a positive control for the markers of pluripotency, and b) Comparing the expression level of a set of pluripotency genes in the target population and in the iPS cells population.

It is considered that the cells of the target population don't express pluripotency genes when the expression levels of the pluripotency genes is below 10%, more preferably below 5% of the expression level of these genes in the iPS cells population, or when less than 10%, more preferably less than 5% of the cells express the gene. Any quantitative method such as RT PCR or flow cytometry, or immune-histo-marking can be used. It is preferred to use FACS (Fluorescence-activated cell sorting) of cells. With this method, less than 10% of the cells of the population shall express these pluripotency genes.

There are multiple markers expressed by a pluripotent cell. In fact, when the cell loses its pluripotency character, it will also lose expression of these markers, as the expression of these pluripotency markers is correlated. Consequently, although multiple genes expressed by pluripotent cells (pluripotency genes) are known in the art, it is not necessary to study a large number of such.

In more details, it is preferred to study the expression of at least one pluripotency gene selected from the group consisting of NANOG, POU5F1 (Oct4), SSEA4, Tra-1-81, and Tra-1-60.

In one embodiment a combination of one intracellular (e.g., OCT4 or Nanog) and one extracellular (e.g., SSEA-4 or Tra-1-60 or Tra-1-81) could be used in order to improve the accuracy of the measure.

However, it is also possible when three of these genes, four or even five genes are looked at.

Determining the percentage of cells expressing these markers in the population is easily performed by the FACS method, with antibodies available in the art. It is even possible to perform this analysis in a multiplex experiment.

When multiple genes are studied, the percentage of cells considered as pluripotent in the population is determined by taking the mean of the percentages of cells harboring each marker.

As an illustration, if the percentage of cells of the given population expressing the gene (1) is 6%, and the percentage of cells of the given population expressing the gene (2) is 5%, it is considered that the population contains 5.5% of pluripotent cells (mean of 5% and 6%) and the given population will be considered as having passed condition (a) above.

In order to determine that the cells of the population express fetal genes and fulfill condition (b), it is necessary to detect genes (markers, proteins or antigens) that are express by the cells when they have entered in one of the differentiation pathway.

Neural Fetal Cells:

Early neural ectoderm progenitors: TP63, MASH1, Notch1, Sox1, Sox2, Musashi 2, Musashi 1, Nestin, Pax6, MUC18, BMI1, Mash1, FABP7, Nucleostemin, Hematopoietic Fetal Cells Hematopoietic mesoderm progenitors: Brachyury (T), MIXL1, cryptic, GATA1, LMO2, ACE, SCL(Tal1), HoxA9, Fli1

Renal Fetal Cells:

Kidney mesoderm progenitors: WT1, HOXD11, SIX2, SALL1, WT1, PAX2, OSR1, PAX8, LHX1, GATA3, HOXB7

Liver Fetal Cells:

Liver endodermic progenitors: SOX17, HNF3B, HNF6, Fox-A2, HNF1B, GATA4, AFP, LGR5

Pancreatic Fetal Cells:

Pancreatic endodermic progenitors SOX17, Fox-A2, CXCR4, GATA4, HNF1B, HNF4A, PDX1, HNF6, PROX1, Ngn3, NeuroD1, PAX6, SYP, SOX9, NKX2-2, NKX6-1, P48, LGR5, HB9

Intestinal Fetal Cells

Intestinal endodermic progenitors: CDX2, TCF-2, SOX 9, NMYC, ID2, SOX2, PAX8, Nkx2.1, LGR5

Lung Fetal Cells

Lung endodermic progenitors: CXCR4, SOX17, FOXA2, NKX2.1, PAX9, TBX1, SOX2 SOX9, ID2, Foxj1, Scgb1a1, Foxj1

Thyroid Fetal Cells

Thyroid endodermic progenitors: CXCR4, SOX17, FOXA2, Pax8, HHEX, Nkx2-1

Other Fetal Cells

Myoblast progenitors: Pax7, Pax3, Myf5

Chondrocyte progenitors: Osteonectin, Sox9.

Osteoblast progenitors: Runx2, ALP, Osx, Osteopontin, Osteocalcin

The genes mentioned above are all known in the art and are specific for each differentiation pathway and for each tissue organoid. These fetal genes in early or late progenitors are not expressed in adult fully differentiated cells. As indicated, their sequence can be found in widely available public databases.

Consequently, these markers are markers of early ontogenetic development and reflect the fact that the cells harboring these markers are not fully adult mature cells. They are still progenitor cells from the fetal developmental phase, meaning that they can still produce various types of mature cells.

In the context of the invention, in order to obtain a fetal cells population, the person skilled in the art shall induce differentiation of pluripotent cells (such as Embryonic Stem cells or iPS cells) within one of the differentiation pathway, according to methods known in the art.

Loss of pluripotency will be verified by checking the loss of expression, in at least 90% of the cells, of the markers as indicated above.

Depending on the differentiation pathway selected by the person of skill in the art, it is possible to check presence of the specific fetal markers indicated above, in the cell population.

To do this, the person skilled in the art will use FACS analysis to measure the percentage of cells expressing the fetal markers of the given pathway, and will calculate the percentage by verifying that at least 70% of the cells express at least one of these markers. Using multiplex FACS analysis also makes it possible to identify the number of cells that express more than one marker. In other words, this means that the percentage of cells that don't express any of these markers is not more than 30%. This is also easily determined by FACS analysis.

It is also possible to determine whether the cell population is a fetal one, even without prior knowledge of the differentiation pathway of the cells.

To check whether a cell population is a fetal cell population according to the invention, one shall first look whether the cells express one or more of the pluripotency markers mentioned above (and the percentage of cells expressing said markers in the population). If less than 10% of the cells express the markers as mentioned above, the person of skill in the art can then look at the expression of fetal markers by the cells of the population.

The morphology/histology of the cells may provide information as to the cell lineage commitment to the person of skill in the art, thus making it possible to select a few markers for a first check. However, it is also possible to verify the fetal nature stage of the cells without pre-knowledge of the cell lineage commitment.

To do so, RNA from the cells of the population can be extracted, reverse transcribed, optionally amplified, and applied to any DNA chip or array that contains probes for fetal markers as mentioned above. One can use, in particular, a Low Density Array (LDA). This makes it possible, not only to determine the presence of fetal markers, but also to qualify these markers, i.e. to determine the differentiation pathway of the cells of the population (depending on the probes that are "turned on" by the RNA from the cell population).

Once the differentiation pathway is known, FACS analysis with the specific markers of this specific cell lineage differentiation pathway can be performed to quantify the percentage of cells expressing these markers in the population.

It has been long suggested that fetal antigens may be expressed in tumor cells (Ting et al, Proc Natl Acad Sci USA. 1972 July; 69(7): 1664-1668).

Such population of fetal cells as disclosed herein for the prophylactic or therapeutic treatment of cancer in a subject. Indeed, the onset and development of cancer may be due or promoted by mutations in the subject cells that induce de-differentiation and make them regress in the differentiation pathway to reach a new "fetal-like" character, and leads to proliferation of such. Consequently, such cells express fetal markers, which are not expressed in mature and fully differentiated adult cells. Furthermore, since these cells divide at a high rate, this induces mutations, that create mutated antigens, also called neo-antigens. It is actually to be noted that the fetal antigens or neo-antigens of tumor cells are generally shared between cancers, at least between cancers of organs originating from the same differentiation pathway (ectoderm, endoderm or mesoderm).

From the ectoderm pathway, the organs are epidermis skin cells, neurons, glial cells, neural crest; pigment cells.

From the mesoderm pathway, the organs are cardiac muscle, skeletal muscle cells, kidney (tubules), red blood cells, smooth muscle (in gut).

From the endoderm pathway, one can cite lung cells (in particular alveolar), thyroid cells, pancreatic cells, hepatic cells.

Finally, the microenvironment of cancer cells is generally favorable to the immune system as it will inhibit the action of T lymphocytes.

Administration of inactivated cells of these fetal cells population, preferably with a HDACi or with a compound increasing expression of MHC-I molecules, will make it possible to induce a immune response against the fetal antigen(s) present on the cells of the population in the subject (preferably a human being, but which can be another mammal, such as a dog, a cat, a cow or a horse), and hence against the tumor cells, thereby leading to regression of the cancer. It is valid for both solid tumors and tumors of the blood.

Indeed, cancer cells can express antigens (markers) such as the ones expressed by the cells of the fetal population herein disclosed and characterized.

Consequently, the population of fetal cells (fetal population) can be used to prime the immune system of a patient, in order for it to be able to adequately and efficiently fight the cancer.

In view of the different pathway, the populations of fetal cells can be used for treatment of lung, pancreas, kidney, breast, blood, gastro-intestinal, thyroid, prostate, brain (in particular glioblastoma) stomach, liver, bone, ovary cancers. One shall choose a population of fetal cells engaged into the same cellular differentiation lineage than the cancer to be treated.

Using such fetal cells population make it possible to deliver at least 10, more generally at least 50, or at least 100, 500, or even 1000 fetal or neo-antigens that are expressed in a given cancer or that are common to different cancers.

The fetal cells can contain mutations that are predisposing to familial cancers that express fetal genes deregulated by this mutation (BRCA, cMET, RET, APC etc.) and that are shared in cancers of the lineage, for instance, a iPS cell obtained from a blood cell containing the c-Met mutation can be derived as a kidney organoid that contains the c-Met mutation present in kidney cancers.

Use of a mutagenic agent when preparing the fetal cell composition (see below) shall introduce mutations (such as missense or frameshift mutations) in the genes of the cells of the population, and thus expression of neo-antigens.

In particular, the inventors have shown that an iPS cell obtained from a cell of a chronic myeloid leukemia (CML), mutated with ENU and derived in hematopoietic fetal cells contains antigens that are present in acute myeloid leukemia (AML).

In order to treat a patient, one can i) obtain an antigen specific signature of the subject's cancer, from a biopsy of such cancer
ii) select a population of inactivated fetal cells that contain cells that express at least one of the antigen determined in step i)
iii) administer this population to the patient, together with an HDACi or an agent that increases MHC-I expression and a TLR3 agonist.

Step i) is performed by methods known in the art, using tools that are available in the art.

The signature is obtained, in particular, by determining the genes expressed in the cancer cells (exome sequencing)
comparing the genes to a database of cancer specific genes (one can cite, in particular the COSMIC database (Catalogue Of Somatic Mutations In Cancer, developed by the Sanger Institute in the UK) or the Cancer Genome Atlas (TCGA, maintained by the NCBI in the US). These databases regroup various sequences coding for antigens expressed in cancer cells
selecting the genes that are present in both the exome and the database as an antigen specific signature of the cancer.

Step ii) is performed by performing an exome of a fetal cell population and verifying that at least one of the genes of the antigen specific signature of the cancer is present in the exome obtained from the fetal cell population.

In another embodiment, one can i) obtain an antigen specific signature of the subject's cancer, from a biopsy of such cancer
ii) select a population of inactivated fetal cells that contain cells that commonly express at least one of the antigen determined in step a
iii) administer an extract of this population to the patient, together with an HDACi or an agent that increases MHC-I expression, and with a TLR3 agonist.

In this embodiment, the extract is selected from total RNA, mRNA, DNA, protein extract, lysate, freeze-dried extract, lyophylisate or dessicate cells, exosomes, extracellular microvesicules, and apoptotic bodies.

In another embodiment, one can i) obtain an antigen specific signature of the subject's cancer, from a biopsy of such cancer
ii) select a population of inactivated fetal cells that contain cells that commonly express at least one of the antigen determined in step i)
iii) administer to the patient a population of T-cells or of antigen presenting cells that have been primed in vitro with the population of ii) or an extract of such population, in presence of an HDACi or an agent that increases MHC-I expression, and of a TLR3 agonist.

In a specific embodiment, said population has been obtained by:

a. Differentiation of a population of pluripotent cells towards the pathway pertaining to the specific cancer of the patient, wherein the pluripotent cells have optionally been expanded in presence of a mutagenic agent,
b. Expansion of the cells thus differentiated
c. Optionally exposition of to a mutagenic agent during expansion, to induce mutagenesis of genes in cells of said population
d. Verification that at least 70% of the cells of the population express fetal markers
e. Optionally verification that the cells of the population express at least one cancer or neo-antigen that is present in the subject's cancer cells,
f. Inactivation of the cells, in order for the cells to lose their ability to divide.

Using a fetal cells population according to the invention is particularly interesting. Indeed, these cells contain a multitude of fetal antigens susceptible to be expressed by cancer cells.

The invention also relates to a method to develop and produce a population of cells intended to be used for the treatment of a cancer in a patient.

The method comprises the steps of a) Optionally performing a biopsy of the cancer
b) Analyzing the cells recovered from a cancer biopsy from the patient to identify fetal and cancer markers expressed by cancer cells
c) Differentiation of a population of pluripotent cells through the pathway pertaining to the specific cancer of the patient (for instance, if the patient has a kidney cancer, differentiation on the kidney pathway will be induced)
d) Optionally introduction of mutations in the population of differentiated cells: such step is optional but preferably performed. It is intended to increase the diversity of the antigens expressed by the cells of the population, to improve the ability of the immune system, upon exposition to the cells, to control the cancer cells even in presence of mutations of the cells thereof. The rate of mutation can be controlled by checking the sequence of one or more genes of the cell population. It is possible to identify the presence of mutated sequences of a given gene within the population and quantify such as compared to the sequences of the gene in the population. For instance, a mutation rate of 0.1% for a given gene indicates that 0.1% of the sequences identified, for this gene, in the population, present a mutation. The mutation rate for a given gene is calculated by sequencing the DNA for the gene, and calculating the percentage of copies that contain a mutation with regards to the native sequence (which is the sequence that is essentially and mainly present (as the predominant sequence is the native "wild-type" sequence).

e) Optionally verifying that the cells of the population express at least one cancer or neo-antigen that is present in the subject's cancer cells, f) Inactivation of the cells, in order for the cells to lose their ability to divide. This is to avoid proliferation of the cells in vivo after all or part of the cell population is administered to the patient Once the cell population has been obtained, of all or part of it can be administered to an animal (preferably a mammal, more preferably a human being), in presence of a HDACi or a compound stimulating expression of MHC-I, and of a TLR3 agonist. As indicated above, in all methods, one can administer the inactivated fetal cell population, or an extract thereof, or T-lymphocytes or antigen presenting cells primed with the population or an extract thereof.

In a specific embodiment, the pluripotent cells of step c) are iPS cells (Induced pluripotent stem cells) that have been developed from cells of the patient. This may reduce the risk of cross-immunity when the fetal cells are administered to the patient. Indeed, the non-fetal antigens shall not be recognized by the immune system, whereas the fetal antigens (present on the cells of the population and on cancer cells) shall be recognized.

Alternatively, the invention relates to a method for treating a patient, comprising the steps of a) Optionally performing a biopsy of the cancer b) Analyzing the cells recovered from a cancer biopsy from the patient to identify fetal and cancer markers expressed by cancer cells c) Selecting a population of inactivated and optionally mutagenized fetal cells engaged in the differentiation pathway pertaining to the specific cancer of the patient d) Administering the cells to the patient, an HDACi or a compound that stimulates or increases MHC-I expression, and a TLR3 agonist.

In a specific embodiment, the fetal cells are engaged in the lung differentiation pathway. They would thus express the markers as indicated above for lung. These cells are particularly adapted for the treatment of lung cancer.

In a specific embodiment, the fetal cells are engaged in the thyroid differentiation pathway. They would thus express the markers as indicated above for thyroid. These cells are particularly adapted for the treatment of thyroid cancer.

In a specific embodiment, the fetal cells are engaged in the kidney differentiation pathway. They would thus express the markers as indicated above for kidney. These cells are particularly adapted for the treatment of kidney cancer.

In a specific embodiment, the fetal cells are engaged in the hematopoietic differentiation pathway. They would thus express the markers as indicated above for hematopoietic cells. These cells are particularly adapted for the treatment of blood cancer (leukemia).

In a specific embodiment, the fetal cells are engaged in the liver differentiation pathway. They would thus express the markers as indicated above for liver. These cells are particularly adapted for the treatment of liver cancer.

In a specific embodiment, the fetal cells are engaged in the intestinal differentiation pathway. They would thus express the markers as indicated above for intestinal. These cells are particularly adapted for the treatment of gastro-intestinal cancer.

In a specific embodiment, the fetal cells are engaged in the pancreatic differentiation pathway. They would thus express the markers as indicated above for pancreas. These cells are particularly adapted for the treatment of pancreatic cancer.

In a specific embodiment, the fetal cells are engaged in the neural differentiation pathway. They would thus express the markers as indicated above for neurons or brain. These cells are particularly adapted for the treatment of brain cancer (in particular glioblastomas).

In a specific embodiment, the fetal cells are engaged in the bone differentiation pathway. They would thus express the markers as indicated above for osteoblast. These cells are particularly adapted for the treatment of bone cancer.

Such elements are disclosed in WO2019101956.

Population of Pluripotent Cells

Pluripotent cells can be Embryonic Stem Cells (ESCs) or Induced Pluripotent Stem Cells (iPSCs), preferably of human origin. However, when the subject is from another species than human, the pluripotent cells are from the subject's species.

As used herein, the term "human Embryonic Stem Cells (hESCs)" refers to isolated cells from a pre-blastocyst stage embryo. In another embodiment, the hES cells are prepared by dedifferentiation of at least partially differentiated cells (e.g., multipotent cells) and are totipotent in practice. Methods of preparing hESC are well known and taught, for example, in U.S. Pat. Nos. 5,843,780, 6,200,806, 7,029,913, 5,453,357, 5,690,926, 6,642,048, 6,800,480, 5,166,065, 6,090,622, 6,562,619, 6,921,632, and 5,914,268, U.S. Published Application No. 2005/0176707, International Application No. WO2001085917. In the context of the invention, the human embryonic stem cells (hESC) are generated without embryo destruction according to the technology as described in Chung et al 2008.

As used herein, the term "human Induced Pluripotent Stem Cells (hiPSCs)" refers to a pluripotent stem cell artificially derived from a non-pluripotent cell by a reprogramming procedure, using methods known in the art and initially disclosed by Yamanaka (in particular WO2012/060473, PCT/JP2006/324881, PCT/JP02/05350, U.S. Pat. Nos. 9,499,797, 9,637,732, 8,158,766, 8,129,187, 8,058,065, 8,278,104. In short, somatic cells are reprogrammed to induced pluripotent stem cells (iPSCs) by ectopic expression of defined factors such as Oct4, Sox2, Klf4 and c-My, or Oct4, Sox2, Lin28 and Nanog. In a particular embodiment, the induced pluripotent stem cells are derived from mammals in particular (but not limited to) rodents, pigs, cats, dogs, and non-human primates, and human.

Preparation of the Cell Population

In a particular embodiment, the membrane of the cells is preserved (so that presentation of the antigen is made through the MHC-I pathway). In a particular embodiment, the cells are inactivated, as described above or below. In a particular embodiment, the cells are human Embryonic Stem Cells (hESCs), human Induced Pluripotent Stem Cells (hiPSCs), fetal stem cells, as described below, cancer stem cells, virus-infected cells or bacterial cells. In another embodiment, the immunogenic element is a cell composition comprising Antigen-Presenting-Cells (APCs) that have been primed in vitro by antigens of interest. This composition is an antigen-presenting cell vaccine, made of antigens and antigen-presenting cells (APCs). Antigen-presenting cells are cells that display antigen complexed with major histocompatibility complexes (MHCs) on their surfaces. One can cite dendritic cells (DC), which are preferred in the context of the invention, as they are able to present antigen to both helper and cytotoxic T cells, macrophages, or B cells. These APCs may be natural cells, or engineered cells. One can, in particular, cite Eggermont et al (Trends in Biotechnology, 2014, 32, 9, 456-465) which review advances in developing artificial antigen-presenting cells. Methods of developing anti-cancer vaccines, using APCs, have been widely proposed in the art and are known by the person skilled in the art.

In another embodiment, the immunogenic element consists in a composition of T cell lymphocytes that have been primed in vitro against the antigen of interest, for instance by exposure to Antigen-Presenting-Cells presenting the antigen of interest. Consequently, this composition is able to onset an immune response in vivo against the antigen of interest. This strategy can be called "adoptive transfer of T cells", and it is known that such adoptively transferred T cells persist for long periods of time in vivo and readily migrate between the lymphoid and vascular compartments (Bear et al, J Biomed Biotechnol. 2011; 2011:417403; Melief et al, J Clin Invest. 2015; 125(9):3401-3412).

In some embodiments, the HDACi is administered in combination with the vaccine composition containing the immunogenic element. Said administration may be simultaneous, separate or sequential, as disclosed below for the embodiment where the immunogenic element is a composition of a population of i) human Embryonic Stem Cells (hESCs), ii) human Induced Pluripotent Stem Cells (hiPSCs) or iii) fetal stem cells.

The present specification emphasizes an HDAC inhibitor (in particular valproic acid), together with a composition of population of i) human Embryonic Stem Cells (hESCs), ii) human Induced Pluripotent Stem Cells (hiPSCs) or iii) fetal stem cells, as such cells express antigens and neo-antigens that are also found in very aggressive cancers, as reminded above. Consequently, whatever the immunogenic element, it is preferred when the antigen of interest is an antigen or a neo-antigen that is expressed by cancer cells, as described above and also below.

In a particular embodiment, the immunogenic element is a cell composition, wherein the population of i) human Embryonic Stem Cells (hESCs), ii) human Induced Pluripotent Stem Cells (hiPSCs) or iii) fetal stem cell composition has been obtained from pluripotent stem cells and inactivation of fetal stem cells, as further disclosed in details below.

In a particular embodiment, the immunogenic element is a cell composition, wherein cell composition has been obtained by in vitro differentiation of pluripotent stem cells (ESC and iPSC) or fetal stem cell composition. More particularly, the immunogenic element is a population of i) human Embryonic Stem Cells (hESCs) composition, ii) human Induced Pluripotent Stem Cells (hiPSCs) composition, or iii) fetal stem cell composition. Typically, the method for producing a population of pluripotent cells or fetal stem cells is described on the following patent applications: WO2017/202949 and EP17306635.8 respectfully.

Typically, the method for producing hESCs or hiPSCs, comprising the steps of: i) expanding pluripotent cells, in the presence of such conditions as to maintain the pluripotent ability of the cells, in the presence of an agent that induces MHC-I presentation of antigens in said population during the expansion step; ii) Exposing the expanded cells to an inactivating agent that will inactivate the cells, iii) Recovering and conditioning the expanded inactivated cells.

Expansion of the cells is performed in conditions so as to maintain the pluripotent ability of the cells (medium, temperature). These culture conditions are known in the art. Maintenance of the pluripotent ability of the cells will ensure that such cells will express (and hence present) all embryonic antigens, thereby increasing the capability of the cells of presenting such antigen at their surface through the MHC I pathway.

The more embryonic antigens presented on the pluripotent cells surface, the increased probability that at least one of these antigens will also be present at the surface of the cancer cells, which will then be recognized and targeted by the immune system that will have been primed by the vaccine composition of the invention.

Hence, maintenance of the pluripotency of the cells of the composition according to the invention, obtained by the methods herein disclosed, leads to presentation of a wide variety of embryonic antigens, and thus to the ubiquitous potency of the vaccine composition of the invention in the treatment methods herein disclosed.

Expansion of the cells in conditions such as to maintain pluripotency is known in the art. It is described, in particular, in all iPSC expansion protocols described to date (Shi Y and al, Nat Rev Drug Discovery 2017; Chen KG and al Cell Stem Cell. 2014). It is preferred when the following conditions are used:

The population of human Embryonic Stem Cells (hESCs), human Induced Pluripotent Stem Cells (hiPSCs), or fetal stem cells are mutagenized cells.

Use of E8 medium or all clinical grade ESC/iPSC culture medium, optionally supplemented with VPA and/or mutagen agents (such as ENU, see below).

Temperature of 37° C. with or without hypoxia conditions

Change of the medium every day using the same medium with addition of VPA (from 0.1 mM to 5 mM) and/or ENU (0.1 μg/ml to 100 μg/ml) and/or p53 inhibitor and/or compound that enhance cell survival such as Y-27632 Rock inhibitor.

The cells are generally cultured for 8 weeks, with an optimal density of 90% maintained by regular passages once a week using enzymatic detachment (collagenase, trypsine).

In a particular embodiment, the pluripotent cells and fetal stem cells that are used in the method of treatment herein disclosed are inactivated. The term "inactivated", and grammatical variants thereof, is used herein to refer to a cell (e.g., a pluripotent cell or a feta stem cell) that is alive but has been rendered incapable of proliferation (i.e., mitotically inactivated). The skilled in the art may use techniques that are known in the art including, but not limited to exposure to chemical agents, irradiation and/or lyophilization. Pluripotent cells and fetal stem cells can be inactivated such that upon administration to a subject the pluripotent cells are incapable of dividing and thus cannot form teratomas in the subject. It is understood that in the context of a plurality of cells, not every cell needs to be incapable of proliferation. Thus, as used herein the phrase "inactivated to an extent sufficient to prevent teratoma formation in the subject" refers to a degree of inactivation in the population as a whole such that after administration to a subject, a teratoma does not form since the irradiated pluripotent stem cells or fetal stem cells did not divide anymore as confirmed by in vitro culture. It is to be noted that, even if a one or more cells in the plurality of cells are in fact capable of proliferation in the subject, it is postulated that the immune system of the host will destroy those cells before a teratoma could form. Such inability of proliferation and teratoma formation may be confirmed by testing in mice having a functional and a non-functional immune system.

In some embodiments, an "inactivated" cell is a killed cell, and in some embodiments, the inactivated cell is a whole cellular lysate, pluripotent stem cells or fetal stem cells derived exosomes, enriched cancer stem neo-antigens, a whole purified cancer stem neo-antigens, DNA RNA and protein extracts, a whole cells suspension that has been lyophilized, a fraction of a cellular lysate such as a membrane fraction, a cytoplasmic fraction, or a combination thereof.

Inactivated pluripotent stem cells or fetal stem cells remain capable of stimulating immune response when the vaccination of mice is carried out with hESCs or hiPSCs in combination with valproic acid or another HDACi. This vaccination is able to induce efficient immune and anti-tumoral responses against 4T1 breast carcinoma without evidence of side effects and autoimmune diseases.

Typically, to inactivate the stem cells, they can be exposed to lethal doses of radiation, (e.g., 5 to 100 Gy single fraction). The precise radiation dose delivered to the cells and length of dose are not critical so long as the cells are rendered nonviable.

The recovery step of the method includes one (or multiple) step(s) of washing the cell culture and resuspending the cells in any appropriate medium such as X-Vivo/Stemflex media or any other clinical grade cell media.

The conditioning of the cells may include freezing or lyophilizing the cells, in order to be able to store the cell composition before use.

It is reminded that pluripotent cells or fetal stem cells are cells that are genetically very stable. Indeed, since they are present very early in the process of embryo development and they must multiply for embryo development, it is important that these cells are not too prone to mutations in order to have homogeneity in the embryo. Consequently cells present in a population of pluripotent cells or fetal stem cells are generally very homogenous when considering their genetic content (i.e. more than 95% of the cells of the population present the same genetic background.

When preparing iPSCs or fetal stem cells, a selective advantage of some cells occur during multiple passages, which leads to the population of iPSCs clones that present particular mutations at late passages, but the sequence of the cell genomes are similar close to 100%.

However, after several passages, iPSC are as stable as hESC (Hussein SM and al, Nature 2011). Culture-induced (adaptive) mutations will be acquired with a very few genetic changes upon prolonged culture (Hussein SM and al, Bioessays, 2012).

It is however, favorable to be able to induce mutations in the cells in order to increase the variability of fetal/embryonic neo-antigens on the treated cellular material that are found in the aggressive cancers. In this way it will increase the possibility for the immune system to generate T cells against these mutated cells and be able to fight cancer cells as well as those that would undergo later variation during growth of the tumor.

This would help to fight the cancer that results from accumulation of genetic alterations resulting from DNA replication errors and/or environmental insults during proliferation of cancer stem cells. These alterations include cancer driver mutations that initiate carcinogenesis and genome destabilizing mutations. This increased genome instability results in clonal evolution leading to the selection of more aggressive clones with increased drug resistance.

Consequently, in a specific embodiment, the cells are expanded in conditions that will induce mutations in genes of said cells.

The cells can thus be exposed to a mutagenic agent, i.e. a physical or chemical agent that changes the genetic material, usually DNA, of an organism and thus increases the frequency of mutations above the natural background level.

The mutagen can be selected from the group consisting of physical mutagens and chemical mutagens.

Among physical mutagens, one can cite ionizing radiations such as X-rays, gamma rays and alpha particles which may cause DNA breakage and other damages. One can, in particular cite radiations from cobalt-60 and cesium-137. The level of irradiating rays shall be much lower the one that is used for cells inactivation and can be designed by the person skilled in the art ultraviolet radiations with wavelength above 260 nm, which can cause error in replication if left uncorrected.

or radioactive decay, such as 14C in DNA.

Among chemical mutagens, one can cite

Reactive oxygen species (ROS), such as superoxide, hydroxyl radicals, hydrogen peroxide.

Deaminating agents, such as nitrous acid which can cause transition mutations by converting cytosine to uracil.

Polycyclic aromatic hydrocarbon (PAH), which can bind to DNA when activated to diol-epoxides.

Alkylating agents such as ethylnitrosourea (ENU, CAS number 759-73-9), mustard gas or vinyl chloride.

Aromatic amines and amides such as 2-Acetylaminofluorene

Alkaloid from plants, such as those from Vinca species

Bromine and some compounds that contain bromine

Sodium azide

Bleomycin

Psoralen combined with ultraviolet radiation

Benzene

Base analogs, which can substitute for DNA bases during replication and cause transition mutations Intercalating agents, such as ethidium bromide, proflavine, daunorubicin Metals, such as arsenic, cadmium, chromium, nickel and their compounds which may be mutagenic The inventors have shown that it is possible to design culture conditions that make it possible to induce DNA replication errors in pluripotent stem cells or fetal stem cells without triggering DNA damage-dependent apoptosis.

This is particularly surprising as, as indicated above, pluripotent cells or fetal stem cells are naturally very stable for there should be as low number as possible mutations introduced during the early stages of embryogenesis. It results from this that the DNA repair machinery is very efficient in these cells, thereby correcting most defects and/or inducing apoptosis in case it is not possible to correct these defects.

In one embodiment, pluripotent cells (such as ESCs or IPSCs) of a starting population are expanded and maintained in pluripotent permissive culture media (as known in the art) to preserve the pluripotent stage during iterative passages. In these conditions, one would generally observe a low amount of exome mutations (5-10 mutations per exome).

The pluripotent cells or fetal cells are then cultured in vitro with mutagenesis compounds methods to induce and increase genomic instability within the pluripotent stem cells or fetal cells, such as the ones listed above. DNA damage is well confirmed by phosphorylation of γH2AX as a marker for Double-Strand Breaks (DSBs). Both proportion of γH2AX positive cells and frequency of γH2AX foci increased in ESCs or IPSCs as well as higher number of micronuclei as a mark of genomic instability.

In a particular embodiment, agents are Bleomycin, ENU, alkylating agents, Actinomycin D, ROS-modulating agents, UV, H2O2, ionizing radiations (gamma rays, X rays), which all allow the induction and enhancement of mutation rates in pluripotent stem cells or fetal cells that accumulate during culture.

In a particular embodiment, N-ethyl-N-nitrosourea (ENU) has been shown to create novel mutations and enhance the level of neo-antigens in treated pluripotent stem cells or fetal stem cells during long term culture at least from 7 to 60 days at a dose of <50 μg/ml. These mutations are similar to those reported in cancer.

In a particular embodiment, the method of the invention, wherein the mutagenic agent is selected from the group consisting of chemical mutagenic agents and radiation mutagenic agent (X-Ray, UV radiation), wherein the mutagenic agent is selected from the group consisting of ENU, reactive oxygen species, deaminating agents, polycyclic aromatic hydrocarbons, aromatic amines and sodium azide. In this embodiment, one will obtain a population of pluripotent stem cells or fetal stem cells in which the cells have random mutations (generally different from cell to cell, thereby leading to a heterogeneous population), in particular in cancer related neo-antigens.

It is thus possible to accumulate a diversity of mutations in response to DNA damage during pluripotent cells or fetal cells proliferation with a high rate of mutations from a selective advantage upon prolonged culture, while maintaining the pluripotency of the cells, in particular when the cells are cultured with HDACi in the medium. The presence of HDACis in culture preserves the increase active histones (H3K4me3 and H3K9ac) and epigenetic mark of pluripotency in response to inducing DNA damage, and the replication and proliferation rate during passages.

In another embodiment of the compositions and methods described herein, mutations are induced in the pluripotent or fetal stem cells through genetic modification of the cells with genes that promote high level of genomic instability. In particular, one can delete or reduce activity of genes or signaling pathways involved in DNA repair and replication, using appropriate inhibitors such as NER/BER/DSBR/MMR inhibitors. These methods that induce genomic instability linked to increased DNA damage may be performed by using "vectors" or by "genetic modification" that inactivate or knock down DNA repair related genes or signaling pathways such as DNA polymerase delta complex, mismatch repair (MMR), base excision repair (BER), Nucleotide excision repair (NER), homologous recombination (HR), DSBR or NEJH. Other examples of DNA repair genes are DNApkC, Ku70, Rad 51, Breal or Brca2.

In other embodiments, pluripotent or fetal stem cells are modified so as to repress apoptosis-associated genes such as p53 by genetic modification or chemical p53 such as Pifithrin-mu, Nutlin-3, Nestin or by using compounds that enhance cell survival such as Y-27632, a selective inhibitor of the p160-Rho-associated coiled kinase (ROCK).

In a particular embodiment, the population of pluripotent cells consists of induced pluripotent stem cells (iPSCs) that were generated from somatic cells, such as cells isolated from a patient, that already contained genomic alterations linked i) to DNA repair diseases including for example Ataxia telangiectasia, Bloom syndrome, Cockayne's syndrome, Fanconi's anemia, Werner syndrome, Xeroderma pigmentosum, Nijmegen breakage syndrome;

ii) to hereditary family cancer syndromes with genomic instability, such Lynch syndrome (hereditary non-polyposis colorectal cancer with mutations in MMR genes including MLH1, MSH2, MSH6, PMS1, and PMS2), Li-Fraumeni with mutation in the TP53 gene or CHEK2, Hereditary Breast and Ovarian Cancer (HBOC) syndrome with deletion or mutation in BRCA1/2 gene, familial adenomatous polyposis (FAP) with mutations in APC gene;

iii) somatic oncogenic induced genomic instability as in CML with a translocation (T 9;22).

In a particular embodiment, the population of mutated pluripotent cells is made of induced pluripotent stem cells and generated from somatic cells containing genomic alterations linked to a disease. Typically, genomic alterations could be a translocation (T9:22), a deletion (BRCA1/2) or mutations (BRCA, RET).

In a particular embodiment, the population of pluripotent stem cells consists of iPSCs generated from cancer cell lines or patient-specific cancer cells.

In another embodiment, the population of ESCs, IPSCs or fetal stem cells is modified genetically to over-express multiple non-random cancer stem related neo-antigens by using «vectors». In particular embodiment, the population of ESCs, IPSCs or fetal stem cells is modified genetically to express multiple mutations and cancer stem cell specific neo-antigens (at least 5) in pluripotent stem cells or in fetal stem cells by "genome editing" technology. The present invention provides compositions and methods providing ESCs, IPSCs or fetal stem cells by introducing of multiple neo-antigens thereof by RNA-guided multiplex genome editing, modification, inhibition of expression and other RNA-based technologies.

The term "genome editing" used here refers to the RNA mediated genetic manipulation including, in particular, a guide RNA for cas9-mediated genome editing. This guide RNA, (gRNA) is transfected along with an endonuclease cas9. The guide RNA provides the scaffold and a spacer sequence complementary to the target. In another embodiment genetic manipulation sequence can be a siRNA or a microRNA sequence designed for gene silencing according to standard methods in the art by the use of Crispr-Cas 9 systems. Compositions and methods for making and using Crispr-Cas systems are known in the art and described, in particular, in U.S. Pat. No. 8,697,359.

In a particular embodiment, the population of pluripotent cells fetal stem cells is treated with alkylating agents. As used herein, the term "alkylating agents" refers to a substance which adds one or more alkyl groups from one molecule to another. This treatment creates new mutations in neo-antigens providing superior immune reactions by increasing oligo clonal expansion of TILs and Th1/Th2 cellular immunity.

In the present invention, an alkylating agent is selected from the group consisting of nitrogen mustards, nitrosoureas, alkyl sulfonates, triazines, ethylenimines, and combinations thereof. Non-limiting examples of nitrogen mustards include mechlorethamine (Lundbeck), chlorambucil (GlaxoSmithKline), cyclophosphamide (Mead Johnson Co.), bendamustine (Astellas), ifosfamide (Baxter International), melphalan (Ligand), melphalan flufenamide (Oncopeptides), and pharmaceutically acceptable salts thereof. Non-limiting examples of nitrosoureas include streptozocin (Teva), carmustine (Eisai), lomustine (Sanofi), and pharmaceutically acceptable salts thereof. Non-limiting examples of alkyl sulfonates include busulfan (Jazz Pharmaceuticals) and pharmaceutically acceptable salts thereof. Non-limiting examples of triazines include dacarbazine (Bayer), temozolomide (Cancer Research Technology), and pharmaceutically acceptable salts thereof. Non-limiting examples of ethylenimines include thiotepa (Bedford Laboratories), altretamine (MGI Pharma), and pharmaceutically acceptable salts thereof. Other alkylating agents include ProLindac (Access), Ac-225 BC-8 (Actinium Pharmaceuticals), ALF-2111 (Alfact Innovation), trofosfamide (Baxter International), MDX-1203 (Bristol-Myers Squibb), thioureidobutyronitrile (CellCeutix), mitobronitol (Chinoin), mitolactol (Chinoin), nimustine (Daiichi Sankyo), glufosfamide (Eleison Pharmaceuticals), HuMax-TAC and PBD ADC combinations (Genmab), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1G cells and ifosfamide combinations (Nuvilex), estramustine phosphate (Pfizer), prednimustine (Pfizer), lurbinectedin (PharmaMar), trabectedin (PharmaMar), altreatamine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), and pharmaceutically acceptable salts thereof. In another embodiment, the alkylating agent is selected from the group consisting of mechlorethamine (Lundbeck), chlorambucil (GlaxoSmithKline), cyclophosphamide (Mead Johnson Co.), streptozocin (Teva), dacarbazine (Bayer), thiotepa (Bedford Laboratories), altretamine (MGI Pharma), pharmaceutically acceptable salts thereof, and combinations thereof. In another embodiment, the alkylating agent is selected from the group consisting of ProLindac (Access), Ac-225 BC-8 (Actinium Pharmaceuticals), ALF-2111 (Alfact Innovation), bendamustine (Astellas), ifosfamide (Baxter International), trofosfamide (Baxter International), MDX-1203 (Bristol-Myers Squibb), temozolomide (Cancer Research Technology), thioureidobutyronitrile (CellCeutix), mitobronitol (Chinoin), mitolactol (Chinoin), nimustine (Daiichi Sankyo), carmustine (Eisai), glufosfamide (Eleison Pharmaceuticals), HuMax-TAC and PBD ADC combinations (Genmab), busulfan (Jazz Pharmaceuticals), melphalan (Ligand), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1 G cells and ifosfamide combinations (Nuvilex), melphalan flufenamide (Oncopeptides), estramustine phosphate (Pfizer), prednimustine (Pfizer), lurbinectedin (PharmaMar), trabectedin (PharmaMar), altreatamine (Sanofi), lomustine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), pharmaceutically acceptable salts thereof, and combinations thereof.

In a particular embodiment, the population of pluripotent cells or fetal stem cells is treated with N-ethyl-N-nitrosourea (ENU, CAS Number 759-73-9). ENU has the following chemical formula $C_3H7N_3O_2$, is a highly potent mutagen by transferring the ethyl group to nucleobases in nucleic acids.

As indicated above, the purpose of the mutagenic agent is to introduce random mutations in genes of the pluripotent cells or fetal cells during expansion (introduction of mutations occurs during the replication and division of the cells). The population of pluripotent stem cell or fetal stem cells acquires mutations that may provide a growth advantage and are selected for to promote culture adaptation. Passages of ESCs, IPSCs or fetal stem cells undergo a high level of selection pressure, and upon expansion multiple clonal mutated populations may be favorably selected for.

It is to be noted that, since the pluripotent cells are very stable, application of the mutagen may have to be performed for a long period of time. As a matter of illustration, when ENU is used, it may be applied for at least 7 days, more preferably at least 15 days, more preferably at least 20 days, more preferably at least 30 days, more preferably at least 40 days, more preferably at least 50 days or even at least 60 days. After application of the mutagen, the cells are washed (if the mutagen is a chemical agent) and can be further expanded, in the presence of the agent that favors MHC-I expression, in particular a HDACi. This agent is preferably also present during application of the mutagenic agent.

It can thus be observed and checked that the mutagen will induce mutations (i.e non-synonymous, nonsense, frameshift, StopGain, splice variant, CNVs, SNVs) in some of the embryogenic genes that are expressed by the pluripotent cells and hence increase the diversity of these antigens (new neo-antigens within the whole genome). This will thus increase the possibility of the vaccine composition with enhanced immunogenicity, able to stimulate a broad immune response against aggressive cancers where there are rapid and frequent mutations.

An efficient immune response may indeed be difficult to obtain for some cancer where clonal expansion of cancer cells occurs with mutations in the antigens expressed by the tumor cells. The immune response would thus depend in the mutational load of the cancer. The generation of random mutations in the pluripotent cell population or fetal stem cells by the use of the mutagen would thus lead to expression of mutated embryonic antigens and increase the diversity of the antigens presented to the immune system upon vaccination.

Consequently, there would already be primed T-cells against mutated antigens that would appear in the cancer cells during division of such cells, which would speed-up and improve the immune response against these cells.

In a particular embodiment, the population of pluripotent stem cells or fetal stem cells is modified genetically to over-express compounds which stimulate immune response by using gene integration within the pluripotent cell genome or fetal stem cells genome. Typically, in the first step, the population of pluripotent stem cells or fetal stem is isolated and expanded. In the second step, the genes of interest are packaged into integrative viral vectors, such as retroviruses or lentiviruses. In the third step, integrative viral vectors containing the interest gene are transferred to the population of stem cells.

In a particular embodiment, the population of pluripotent cells or fetal stem cell is modified with the genes of proteins which stimulate MHC expressions and/or immune response. These compounds are selected from the group consisting of interferon alpha (IFN-a), an interferon gamma (IFN-γ), an interleukin 2 (IL-2), an interleukin 4 (IL-4), an interleukin 6 (IL-6), an interleukin 12 (IL-12), a tumor necrosis factors (TNFs), and a granulocyte-macrophage colony stimulating factor (GM-CSF), functional fragments thereof, and combinations thereof.

Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behavior and/or increasing their production of antigens thus making the cancer cells easier for the immune system to recognize and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention.

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin).

As used herein, the term "adjuvant" refers to any compounds able to strengthen the immune response against immunogenic antigens and able to increase the recruitment of Antigens Presenting Cells. Such adjuvant is able to activate APC and enhance antigen presentation, induce the expression of inflammatory cytokines and a pro-inflammatory environment, prime naive T cells to drive acquired immunity, modulate adaptive immune reactions, act as immunopotentiators by exhibiting immune stimulatory effects during antigen presentation and by inducing the expression of co-stimulatory molecules on APC, improve the quality of the downstream T helper cytokine profiles and the differentiation of antigen-specific T helper populations, produce from B cells specific antibodies against those antigens. Typically, the adjuvant is selected from the group consisting of but not limited to: i) agonists of toll-like receptors (TLRs): TLR1, TLR2, TLR3, TLR4 (e.g. GLA, MPLA), TLR5, TLR6, TLR7, TLR8 (e.g. VTX-2337), TLR9 (e.g. IC-31; IM-2125,SD-101, ODN2395, ODN 1826), TLR10 TLR11, C-type lectin-like receptors; retinoic acid-inducible gene-like receptors, nucleotide-binding oligomerization domain-like receptors, nucleotide-binding domain and leucine-rich repeat (LRR) containing proteins (NLRs), RIG-I-like receptors (RLR); ii) GM-CSF, IL2, IFN alfa-2a, IFN alfa-2b; iii) aluminum salts, Aluminum hydroxide (alum), IFA, Montanide®, MF59®, QS21 (e.g. QS21 STIMULON), QS21 saponins, QS21 iscomatrix, MPL+ Alum (AS04®), Liposomes, trehalose-6,6', dibehenate (TDB), Complete Freund's Adjuvant (CFA), lipopolysaccharide (LPS), Pam3CysSerLys4 (Pam3CSK4). In a particular embodiment, the adjuvant is an agonist of TLR3. As used herein, the term "TLR3" refers to Toll-like receptor 3. TLR3 agonists are well known by the man skilled in the art. It refers to an affinity agent (i.e., a molecule that binds a target molecule) capable of activating a TLR3 polypeptide to induce a full or partial receptor-mediated response. For example, an agonist of TLR3 induces TLR3 dimerization/oligomerization and triggers TLR3-mediated signaling, either directly or indirectly. A TLR3 agonist, as used herein may, but is not required to, bind a TLR3 polypeptide, and may or may not interact directly with the TLR3 polypeptide. They include double stranded ribonucleic acid (dsRNA) such as: Poly(A:U) for Polyadenylic-polyuridylic acid, Poly (I:C) for Polyinosine-polycytidylic acid, Poly(ICLC) (Hiltonol®), PolyI:PolyC12U (Ampligen®) or RGIC dsRNA such as RGIC 100.1 (Riboxx®).

Such TLR3 agonists are for example described in the U.S. Pat. No. 8,409,813, in particular in columns nine to twenty two, in the patent EP2281043, in the patent application WO2015/091578 and in the patent application WO2008/109083. In particular, the RGIC100.1 is described in examples 1 and 2 of WO2015/091578.

In a particular embodiment, the agonist of TLR3 is Poly (A:U).

As used herein the terms "administering" or "administration" refer to the act of injecting or otherwise physically delivering a substance as it exists outside the body (e.g., combined preparation) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof. As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different.

In particular embodiment, the vaccine composition (pluripotent stem cells or fetal stem cells+agent stimulating MHC presentation+adjuvant) is injected subcutaneously. Injection may be simultaneous, sequential, separate, at the same injection point or at different injection points, in the same syringe, or in separate syringes.

In a particular embodiment, the follow-up treatment (administration of the compound that stimulates MHC I and/or immune system, such as an HDACi, in particular VPA) is administered by the oral route.

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The vaccine composition contains an immunogenic element intended to make the subject develop an immune response against one or more antigen(s) of interest. An antigen of interest are any antigen against which an immune response is desired, and include any peptide, protein either from the self (such as antigens from cancer cells) or exogenous such as bacterial, viral, or parasitic protein, other kind of antigens such as nucleic acids, sugars, lipopolysaccharides and the like.

The method herein described may also comprise the step of administering an HDACi for a few days after the administration of the vaccine composition. This continuous administration of an HDACi can be useful for maintaining the microenvironment modification for a time long enough for the immune cells to be able to "take over" the tumor. Generally, this further continuous administration of the HDACi will consist in a daily administration of an adequate dose of the HDACi, for at least three days following vaccine administration, and up to one month. It is, however preferred when the further HDACi administration is performed for at least one week, more preferably at least or about two weeks.

The method according to the invention, wherein the treatment is a prophylactic treatment.

Pharmaceutical and Vaccine Compositions

The population of pluripotent stem cells or fetal stem cells as described above can be used in a vaccine composition. Accordingly, in another aspect, the present invention relates to a vaccine composition comprising i) a population of human embryonic stem cells (hESCs), human Induced Pluripotent Stem Cells (hiPSCs) or fetal stem cells, ii) agent that induces MHC-I presentation of antigen (e.g. HDACi) and iii) an adjuvant.

In particular, such population of human embryonic stem cells (hESCs), human Induced Pluripotent Stem Cells (hiPSCs) or fetal stem cells are inactivated, and optionally mutated in order to suppress their proliferation ability and optionally obtain cell extracts.

In a particular embodiment, the vaccine composition according to the invention, wherein the population of human Embryonic Stem Cells (hESCs), human Induced Pluripotent Stem Cells (hiPSCs), or fetal stem cells are mutagenized cells.

In a particular embodiment, the agent that stimulates immune response a HDACi (used at a dose range comprised between 0.2 mM and 4 mM). In another embodiment, the adjuvant in the context of the invention is an agonist of TLR3.

In a particular embodiment, the HDACi is VPA.

In a particular embodiment, the agonist of TLR3 is Poly(A:U).

The invention also relates to a device (such as a syringe) containing such vaccine composition, that can be used for a simultaneous administration of the HDACi compound, adjuvant and the cell composition.

In a particular embodiment, the vaccine composition of the invention for use in the treatment of a subject suffering from a cancer.

Such vaccine composition can be used as a therapeutic vaccine against cancer cells (cancer cells of which express immunogenic neo-antigens, driver or passenger mutations, progenitors as epigenetically de-differentiated cells, tumor initiating cells expressing fetal and embryonic genes), for cure of the subject, or as a prophylactic vaccine, to prevent onset of such cancers, in particular in subjects susceptible to these cancers. Predisposition genes are, for instance (see also Lindor et al, 2008 Journal of the National Cancer Institute Monographs, No. 38, Concise Handbook of Familial Cancer Susceptibility Syndromes, Second Edition):

Breast/ovary: BRCA1, BRCA2, PALB2, RAD51
Lynch syndrome: MLH1, MSH2, MSH6, PMS2, EPCAM
Hereditary Papillary Renal Cell Carcinoma: FH, MET
Cowden disease: PTEN, PIK3CA
Fanconi disease: FANC
Von Hippel-Lindau disease: VHL
Malignant melanoma: CDKN2A, MITF, BAP1, CDK4
Endocrine Neoplasia: MEN1, RET, CDKN1B
Neurofibromatosis: NF1, NF2, LZTR1, SMARCB1, SPRED1
Hereditary pheochromocytome paragangliome: SDH, TMEM127, MAX, EPAS1
Familial adenomatous polyposis: APC, MUTYH
Retinoblastoma: RB1
Birt-hogg-dub6 syndrome: FLCN
Bloom syndrome: BLM
Carney syndrome: PRKAR1A
Gorlin syndrome: PTCH1
Li-Fraumeni syndrome: TP53, CHEK2
Nijmegen syndrome: NBN
Peutz-Jeghers Syndrome: STK11
Familial Juvenile Polyposis: BMPR1A, SMAD4
Xeroderma pigmentosum: XP
This list is not limitative.

In certain embodiments, the cancer stem cell vaccine product comprises a mixture of cell lysate after lyophylisation, a mixture of enriched multi-cancer stem neoantigens, purified cancer stem neo-antigens, exosomes derived from fetal stem cells, DNA, RNA, proteins or multiple peptides from the population of human embryonic stem cells (hESCs), human Induced Pluripotent Stem Cells (hiPSCs) or fetal stem cells. These are the immunogenic agent as disclosed above, which are formulated in the presence of HDACi.

In another embodiment, cancer stem cell vaccine product is mixed with supernatant GMP media from engineered irradiated population of human embryonic stem cells (hESCs), human Induced Pluripotent Stem Cells (hiPSCs) or fetal stem cells used as an adjuvant effector.

In a particular embodiment, the derived population of human embryonic stem cells (hESCs), human Induced Pluripotent Stem Cells (hiPSCs) or fetal stem cells fetal cells in this composition are inactivated (i.e. can not proliferate anymore).

The composition of derived population of human embryonic stem cells (hESCs), human Induced Pluripotent Stem Cells (hiPSCs) or fetal stem cells fetal stem cells and organoids of the invention is susceptible to be obtained by any of the methods as disclosed above.

It is to be noted that the derived population of human embryonic stem cells (hESCs), human Induced Pluripotent Stem Cells (hiPSCs) or fetal stem cells in this composition are genetically heterogeneous, carrying specific somatic mutations when the mutagen has been used, and hence, differ from a derived population of human embryonic stem cells (hESCs), human Induced Pluripotent Stem Cells (hiPSCs) or fetal stem cells fetal cell composition that has been produced according to methods known in the art, and which is genetically more homogenous.

In a particular embodiment, an HDACi and a DNA methyltransferase inhibitor are both used. Indeed, it has been shown that the combined use of VPA and 5-Azacytidine (an analog of the nucleoside cytidine which can be incorporated into DNA and RNA) leads to a synergetic effect on the re-expression of neo anti-embryonic antigens.

The HDACi is administered in a therapeutically efficient amount. For VPA, it may be from 10 to 15 mg/kg/day, up to 60 mg/kg/day. The plasma level of VPA should preferably be in the usually accepted therapeutic range (50 to 100 μg/mL).

In a particular embodiment, the method according to the invention comprises further one or more of radiation therapy, targeted therapy, immunotherapy, or chemotherapy. Typically, the physician could choose to administer the subject with i) a population of fetal stem cells and ii) a compound selected from a group which activates MHC expression and/or immune response, as a combined preparation with radiation therapy, targeted therapy, immunotherapy, or chemotherapy.

In some embodiments, the subject is administered with i) population of human embryonic stem cells (hESCs), human Induced Pluripotent Stem Cells (hiPSCs) or fetal stem cells, ii) a compound selected from a group which activates MHC expression and/or immune response and iii) an adjuvant, as a combined preparation and a chemotherapeutic agent.

The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaorarnide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the subject is administered with i) a population of human embryonic stem cells (hESCs), human Induced Pluripotent Stem Cells (hiPSCs) or fetal stem cells, ii) a compound selected from a group which activates MHC expression and/or immune response and iii) an adjuvant, as a combined preparation and a targeted cancer therapy.

Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signalling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), bevacizumab (avastin), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the subject is administered with i) population of human embryonic stem cells (hESCs), human Induced Pluripotent Stem Cells (hiPSCs) or fetal stem cells, ii) a compound selected from a group which activates MHC expression and/or immune response and iii) an adjuvant (in particular a TLR3 agonist), as a combined preparation and an immune checkpoint inhibitor.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD1 with its ligands PDL1 and PDL2 (Pardoll, Nature Reviews Cancer 12: 252-264, 2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies. In some embodiments, the immune checkpoint inhibitor is an antibody selected from the group consisting of anti-CTLA4 antibodies (e.g. Ipilimumab), anti-PD1 antibodies (e.g. Nivolumab, Pembrolizumab), anti-PDL1 antibodies, anti-TIM3 antibodies, anti-LAG3 antibodies, anti-B7H3 antibodies, anti-B7H4 antibodies, anti-BTLA antibodies, and anti-B7H6 antibodies. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675, 206). In some embodiments, the anti-CTLA-4 antibody is ipilimumab (also known as 10D1, MDX-D010) a fully human monoclonal IgG antibody that binds to CTLA-4. Another immune checkpoint protein is programmed cell death 1 (PD-1). Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments, the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94). In some embodiments, the immunotherapeutic treatment consists of an adoptive immunotherapy, as described by Nicholas P. Restifo, Mark E. Dudley and Steven A. Rosenberg ("Adoptive immunotherapy for cancer: harnessing the T cell response, Nature Reviews Immunology, Volume 12, April 2012). In adoptive immunotherapy, the patient's circulating lymphocytes, or tumor-infiltrated lymphocytes, are isolated in vitro, activated by lymphokines such as IL-2 and readministered (Rosenberg et al., 1988; 1989). The activated lymphocytes are most preferably be the patient's own cells that were earlier isolated from a blood sample and activated (or "expanded") in vitro. This embodiment is particularly preferred as the HDACi may increase expression of PDL1 on the surface of the cancer cells.

In some embodiments, the subject is administered with i) population of human embryonic stem cells (hESCs), human Induced Pluripotent Stem Cells (hiPSCs) or fetal stem cells, ii) a compound selected from a group which activates MHC expression and/or immune response and iii) an adjuvant (in particular a TLR3 agonist), as a combined preparation and a radiotherapeutic agent.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

In another embodiment, the compounds which activate MHC expression and/or immune response, an adjuvant and the population of population of human embryonic stem cells (hESCs), human Induced Pluripotent Stem Cells (hiPSCs) or fetal stem cells, as described above may be combined with pharmaceutically acceptable excipients, and optionally sustained-release matrices, such as biodegradable polymers, to form pharmaceutical compositions.

The invention further comprises i) a population of population of human embryonic stem cells (hESCs), human Induced Pluripotent Stem Cells (hiPSCs) or fetal stem cells; ii) a compound selected from a group which activates MHC expression and/or immune response and iii) an adjuvant.

The pharmaceutical composition of the invention is used for therapy.

The pharmaceutical composition of the invention is used for treating a cancer.

The pharmaceutical composition of the invention, wherein, the compound selected from a group which activates MHC expression and/or immune response is HDACi.

The pharmaceutical composition of the invention, wherein, the adjuvant is an agonist of TLR3.

In a particular embodiment, the vaccine composition according to the invention comprises i) a population of human embryonic stem cells (hESCs), human Induced Pluripotent Stem Cells (hiPSCs) or fetal stem cells, ii) VPA and iii) Poly(A:U).

In a particular embodiment, the pharmaceutical composition according to the invention comprises i) a population of human embryonic stem cells (hESCs), human Induced Pluripotent Stem Cells (hiPSCs) or fetal stem cells, ii) VPA and iii) Poly(A:U).

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

More particularly, the population of population of population of human embryonic stem cells (hESCs), human Induced Pluripotent Stem Cells (hiPSCs) or fetal stem cells and the compound which activates MHC expression and/or immune response are formulated on a vaccine composition. Accordingly, the invention relates to a vaccine composition comprising i) a population of population of human embryonic stem cells (hESCs), human Induced Pluripotent Stem Cells (hiPSCs) or fetal stem cells, ii) a compound selected from a group which activates MHC expression and/or immune response and iii) an adjuvant.

In a particular embodiment, the vaccine composition according to the invention comprising i) a population of population of human embryonic stem cells (hESCs), human Induced Pluripotent Stem Cells (hiPSCs) or fetal stem cells ii) acid valproic and iii) an agonist of TLR3.

In a particular embodiment, the vaccine composition according to the invention comprising i) a population of population of human embryonic stem cells (hESCs), human Induced Pluripotent Stem Cells (hiPSCs) or fetal stem cells expressing neo-antigens, in particular enhanced by mutagen agents or genetic modification ii) valproic acid and iii) Poly(A:U).

The composition may also comprise 5 Azacytidine.

Moreover, the vaccine composition of the present invention can be used in a subject suffering from a cancer as described above.

The vaccine composition according to the invention can be formulated with the physiological excipients set forth above in the same manner as in the immunogenic compositions. For instance, the pharmaceutically acceptable vehicles include, but are not limited to, phosphate buffered saline solutions, distilled water, emulsions such as an oil/water emulsions, various types of wetting agents sterile solutions and the like. Adjuvants such as muramyl peptides such as MDP, IL-12, aluminium phosphate, aluminium hydroxide, Alum and/or Montanide® can be used in the vaccines.

The vaccine composition according to the invention can be administered subcutaneous (s.c), intradermal (i.d.), intramuscular (i.m.) or intravenous (i.v.) injection, oral administration and intranasal administration or inhalation. The administration of the vaccine is usually in a single dose. Alternatively, the administration of the vaccine of the invention is made a first time (initial vaccination), followed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 32, 33, 34,35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77,78, 79, 80, 81, 82, 83, 84, 85, 86, 87, 88, 89, 90, 91, 92, 93, 94, 95, 96, 97, 98, 99 or 100 recalls (subsequent administration), with the same population of stem cells, the compound which stimulates the immune system or a combination of thereof and/or with a further one or more of radiation therapy, targeted therapy, immunotherapy, or chemotherapy.

The vaccine composition is also provided in a kit. The kit comprises the vaccine composition according to the invention and an information leaflet providing instructions for immunization. The kit comprises also the all materials for the administration of the products.

In summary, the inventors demonstrated that a TLR-3 agonist can be used to potentiate the anti-cancer activity of a vaccine comprising an antigenic composition administered with a HDAC inhibitor (potentially also with a check-point inhibitor).

The antigenic composition comprises inactivated cells (either pluripotent cells or fetal cells that have been inactivated preferably after having been mutagenized). Using these types of cells makes it possible to have a ubiquitous vaccine (when using pluripotent cells) or a more specific vaccine (when using fetal cells engaged in the differentiation pathway of the cancer to be treated), expressing neo-fetal antigens that will be present on the surface of the cancer cells. The presence of the HDAC inhibitor (and its ability to increase MHC-I expression), as well as of the TLR-3 agonist potentiate the cytotoxic T-cell response. Such response can also be improved by the use of a checkpoint inhibitor, which may further increase the response, in particular as HDAC inhibitor may increase expression of PDL-1 (Programmed death-ligand 1 or CD274) which may restrict immune response. However, as shown in the examples, despite such effect of the HDACi, the combination herein disclosed is able to control the cancer proliferation even in the absence of a checkpoint inhibitor.

The invention will be further illustrated by the following figures and examples. However, these examples and figures should not be interpreted in any way as limiting the scope of the present invention.

FIGURES

FIG. 1: Vaccination study with hESC combined with Valproic acid (VPA), Poly(A:U), ODN 2395 or Quil-A® adjuvant on 4T1 mice model. Vaccination study with hESC combined with Valproic acid (VPA), Poly(A:U), ODN 2395 or Quil-A® adjuvant on 4T1 mice model. Blab/c mice two boosts of vaccine containing 3 different adjuvants the day of tumor challenge. Tumor growth was assessed until 26 days to follow the tumor size using calipers permitting to measure both the longitudinal (a, mm) and transverse (b, mm) diameters. Tumor volume was calculated and plotted using calculation formula 1/6Π(a+b/2)3 mm3.

Figure 2:
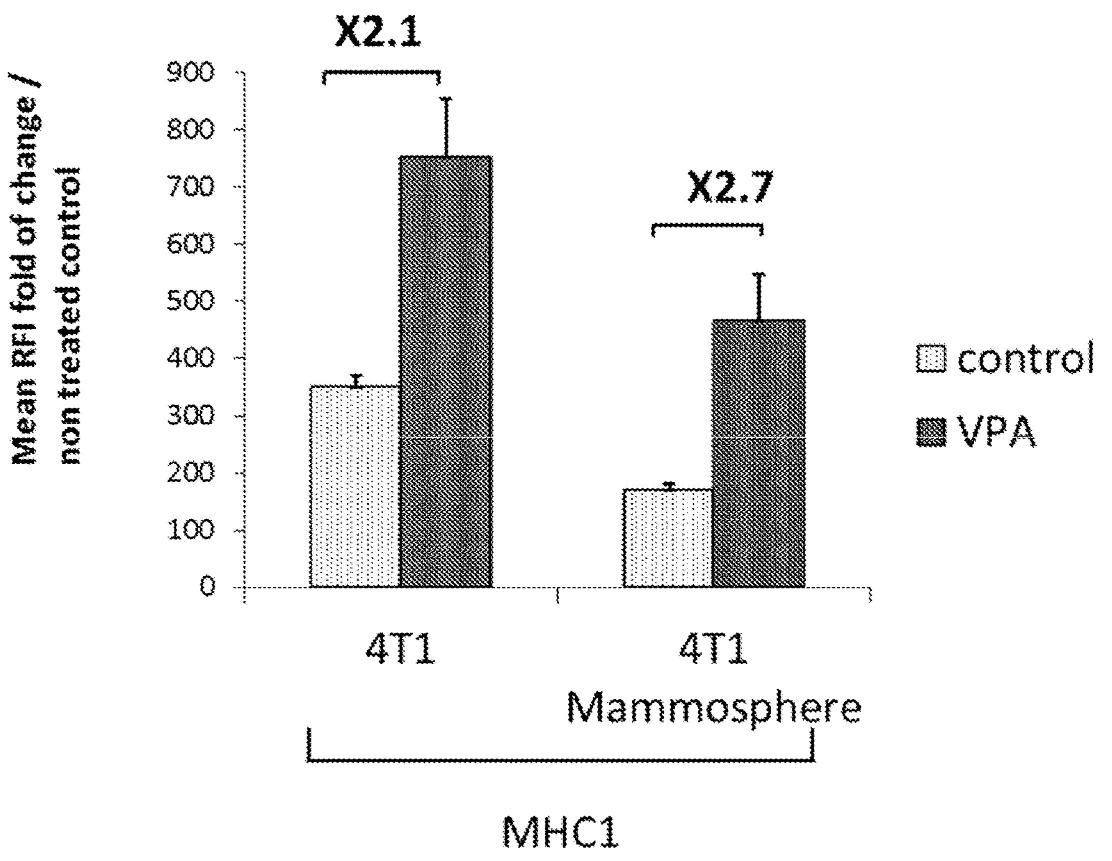

FIG. 2: Valproic acid treatment increases MHC I expression in breast tumor cells. Variation in MHC I expression during VPA treatment at 2 mM on 4T1 adherent cells and on 4T1-derived mammospheres.

Figure 3:
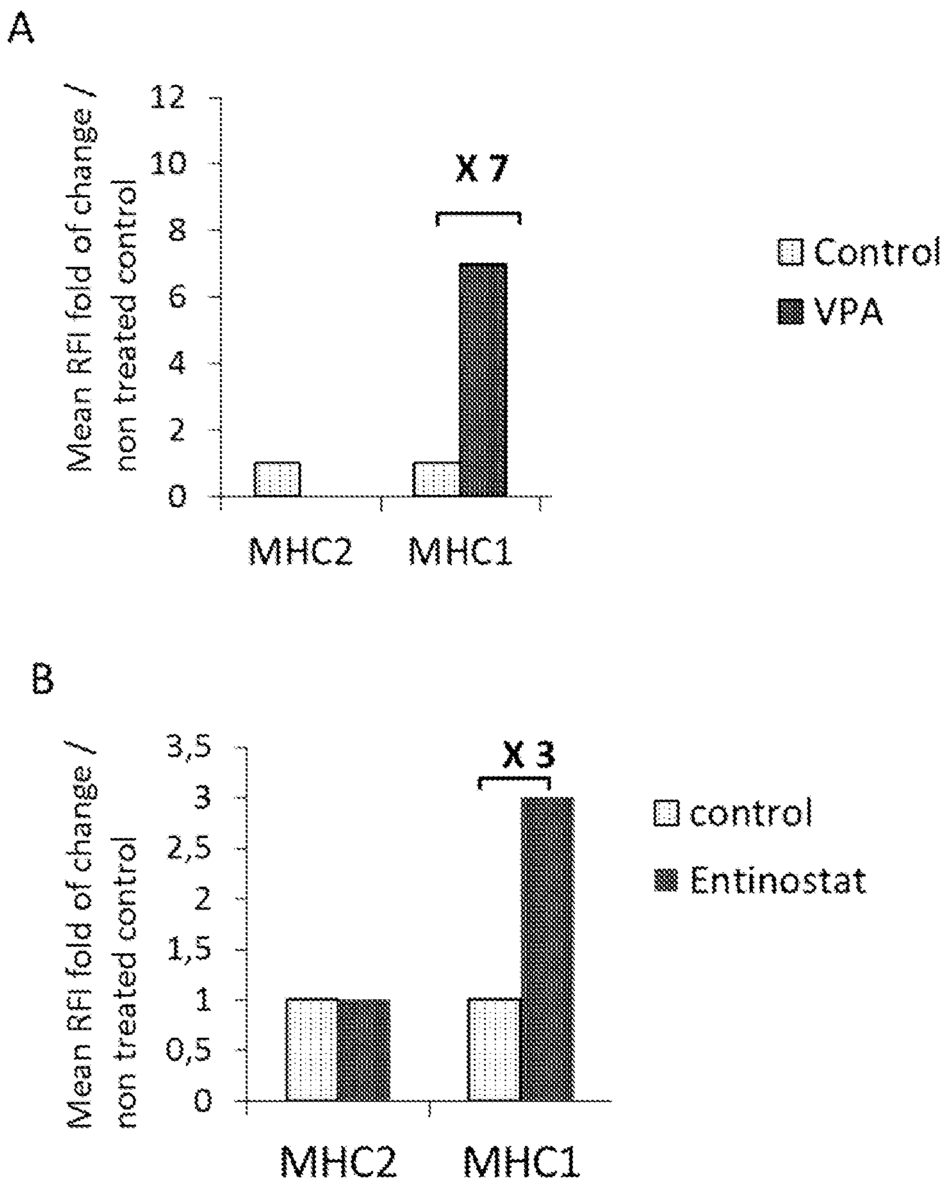
Figure 3:
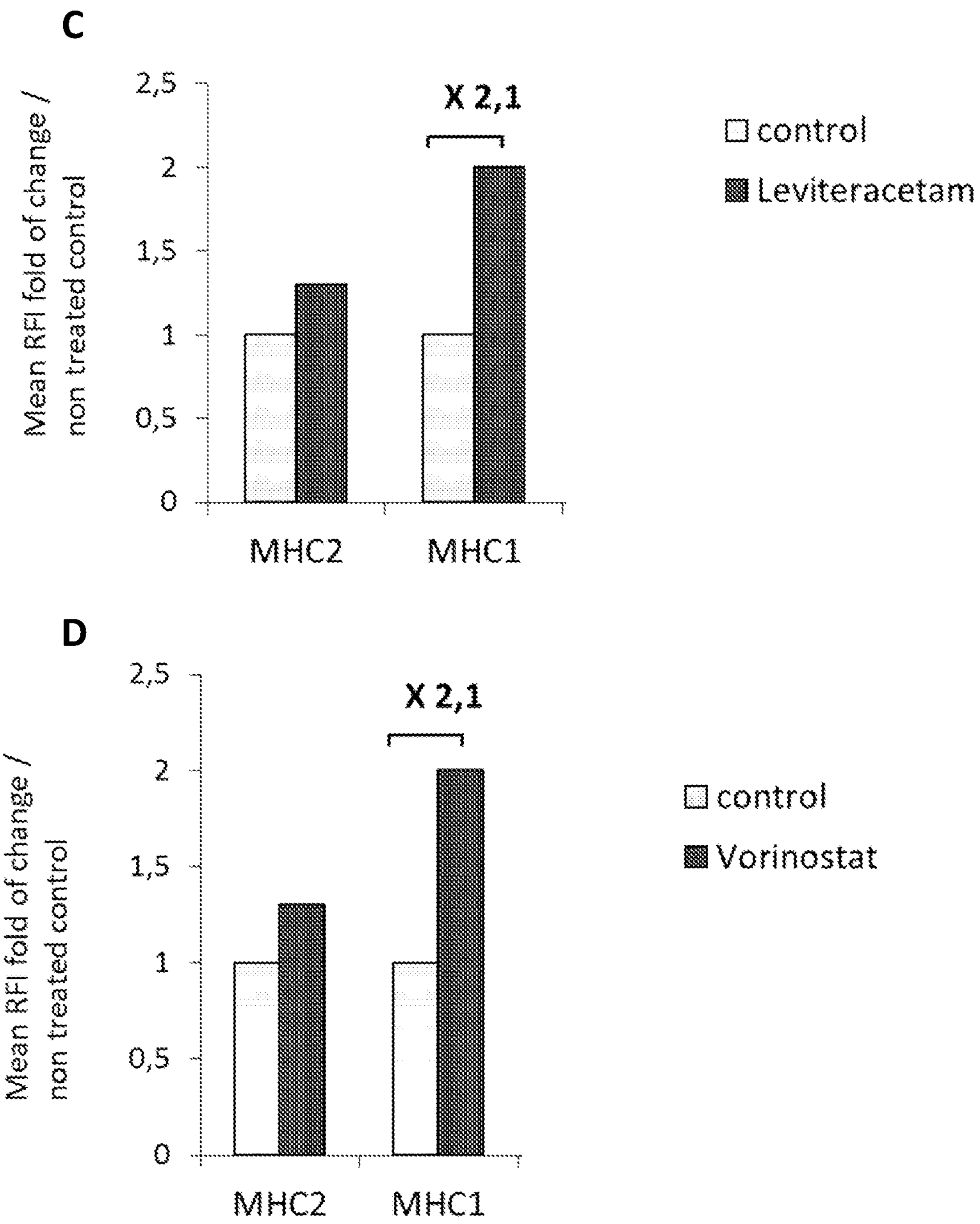

FIG. 3: HDACi up-regulates MHC1 in Lung cancer cell lines. Effects of VPA, Leviteracetam, Vorinostat and Entinostat on the LLC1 immunogenicity. MHCI and MHCII expression was quantified by flow cytometry analysis measuring the Relative Fluorescence Intensity (RFI). LLC1 were treated for 48 hours with Valproic Acid (A), Entinostat (B) Levetiracetam (C) and Vorinostat (D) at the dose corresponding to the IC50.

EXAMPLES

Example 1

The experiment was carried out as followed: Five mice per group received two boosts of vaccine 7 and 14 days with $2\times10^6$ irradiated hESCs cells that were mixed with 3 different adjuvants: 500 µg of TLR3, 50 µg of TLR9 agonist or 50 µg/ml of Quil-A® Saponin vaccine adjuvant. After 14 days $5\times10^4$ 4T1 cells were injected into the mammary fat pad of the mice and Valproic acid added in the drinking water at the dose of 4 mg/ml. Five mice receiving no treatment were used as control. The protocol is summarized in Table 1.

TABLE 1

Experimental timeline and treatment schedule (H9 irradiated hESC vaccine + adjuvants; 4T1 challenge; VPA in drinking water).

| Day 14 | Day 7 | Day 0 |
|---|---|---|
| 1st Boost $2 \times 10^6$ cells (H9) + Adjuvants | 2nd Boost $2 \times 10^6$ cells (H9) + Adjuvants | Challenge ($5 \times 10^4$ 4T1 cells) Mammary fat pad + HDACi (VPA) |

Adjuvants used in the vaccine product: Three different adjuvants were tested:

1/ A TLR3-based adjuvant: Poly(A:U) (ref #tlrl-pau, InvivoGen) Polyadenylic-polyuridylic acid (poly(A:U)) is a synthetic double stranded RNA molecule that specifically signals through TLR3. Poly(A:U) is known to induce the activation of dendritic cells and T lymphocytes, to promote antigen-specific Th1-immune responses and to boost antibody production. The potent adjuvant activity of poly(A:U) has been exploited and approved in the treatment of breast cancers that express TLR3 (Conforti R. et al., 2010. Opposing effects of toll-like receptor (TLR3) signaling in tumors can be therapeutically uncoupled to optimize the anticancer efficacy of TLR3 ligands. Cancer Res. 70(2):490-500).

2/ TLR9-based adjuvant: ODN 2395 VacciGrade™ CpG ODN, type C (ref #vac-2395-1. InvivoGen) ODN 2395 is a type C CpG ODN composed by a synthetic oligodeoxynucleotides (ODNs) containing unmethylated CpG motifs (CpG ODNs) that are mainly found present in bacterial DNA. CpG ODNs are recognized by murine TLR9, which is expressed exclusively on human B cells and dendritic cells, thereby inducing Th1-dominated immune responses. ODN 2395 that activate specifically mouse TLR9 is a potent inducer of IFN-α from dendritic cells and a strong B cell activators.

3/ Quil-A® Saponin vaccine adjuvant (ref #vac-quil InvivoGen). Quil-A® adjuvant is a saponin adjuvant containing the water-extractable fraction of saponins from the South-American tree, *Quillaja saponaria Molina*. Saponins induce a strong adjuvant response to T-dependent as well as T-independent antigens and induce strong cytotoxic CD8+ lymphocyte responses. When combined with cholesterol and phospholipids to form immunostimulatory complexes. Quil-A® adjuvant can activate both the cell-mediated and the antibody-mediated immune responses to a broad range tumor antigens.

Results

We discovered that in contrast to the non-vaccinated mice, the mice vaccinated with hESC combined with a TLR3 agonist have generated the highest reduction of breast tumor volume ($p<0.001$) compared to the use of a TLR9 agonist or to Quil-A® Saponin vaccine adjuvants (FIG. 1).

The reduction rate of tumor growth, with statistically significant differences in the average Tumor size are shown in table 1.

TABLE 1

Percentage of tumor reduction at day 26 compared to the control group receiving only PBS and statistical test (Student test).

| | % of reduction | P value |
|---|---|---|
| VPA | 24 | $p < 0.05$ |
| ODN2395 | 22 | $p < 0.05$ |
| Quil-A | 20 | $p < 0.05$ |
| Poly(A:U) | 54 | $p < 0.001$ |

Throughout this application, various references describe the state of the art to which this invention pertains. The disclosures of these references are hereby incorporated by reference into the present disclosure.

Example 2: Ability for a Compound to Increase MHC I

A compound can be assessed for its ability to increase MHC I on tumor cells (and thus suitable in the context of the present methods) on tumor cells.

Valproic Acid Increases MHC I on Breast Cancer Cells

4T1 cells are a triple negative breast cancer cell line that was incubated with increased doses (0.2 and 2 mM) of valproic acid (VPA). After 4 days of treatment, the MHC I surface marker was quantified by flow cytometry analysis. VPA has the propriety of increasing MHC I levels in a dose-dependent manner highlighting that VPA can enhance an anti-tumor immune response by improving T cell tumor recognition. Furthermore, Relative Fluorescence Intensity (RFI), measured with flow cytometry analysis, revealed an increase of MHC I expression by 2.1- and 2.7-fold in 4T1 and mammosphere-derived 4T1 cells respectively when treated with 2 mM of VPA (FIG. 2). These results suggest that VPA treatments efficiently enhance MHC I expression in both baseline and "stem-cell-like" contexts.

In addition, when 4T1 cells were treated with 2 mM of VPA, we also observed a 2.1-fold increase in PDL1 expression, contrasting with PDL2 expression which was only weakly upregulated after VPA treatment (FIG. 2)

HDAC Inhibitor Increases MHC1 Expression in Lung Tumor Cells

Non-small cell lung cancer (NSCLC) cell line (lewis lung carcinoma, LLC) expressing a particularly aggressive metastatic phenotype was used. Four HDAC inhibitors molecules were evaluated: Entinostat, Levetiracetatm, Vorinostat (Zolinga®) and valproic acid (VPA) (Depakine®), for the expression of Major Histocompatibility Complex (MHC) Class I and II using Flow cytometry analysis.

The half maximal inhibitory concentration (IC50) was first determined for each HDACi using an MTT cell proliferation assay. LLC1 was treated with an increasing dose of HDCAi and proliferation was estimated measuring the absorbance after the incorporation by the cell of MMT (3-(4,5-dimethylthiazol-2-yl)-2,5-diphenyl tetrazolium bromide) substrate. The IC50 (levels) for Vorinostat, Entinostat and Levetiracetam were between 2 and 4 µM and around 2 mM for valproic acid.

LLC1 treated with the 4 HDACi with the dose corresponding to IC50 were shown to modify the MHC class I expression for all HDACi tested. Vorinostat, Levetiracetam, Entinostat and VPA have the propriety of significantly increasing the expression of MHC1 on the cell membrane by 2-fold compared to untreated cells in contrast to MHC class 2 expression that was not modulated at with dose (FIG. 3).

VPA was shown to overexpress MHC1 10 folds more than non-treated LLC1 cells (FIG. 3A).

It is also to be noted that some HDACi increased PDL-1 on the surface of the cells (data not shown).

Example 3: 4T1 Cells Treated with Valproic Acid (VPA) Induced an Upregulation of the Immune Response To determine the effect of VPA on 4T1 cells, a transcriptome analysis on cells treated with 0.5 mM of VPA for 10 days was performed and compared with that of non-VPA treated cells. These analyses allowed for the identification of the set of genes implicated in TNF-α signaling and in the response of IFN-α and IFN-γ. In addition, the use of the SAM algorithm allowed for the discrimination of 44 immune-related genes between the VPA-treated samples and their control counterparts, which were validated by principal component analysis (p-value=$3.3\times10^{-4}$). Among these 44 immune-related genes, CD74, CCL2 and TNFRSF9 were found to be overexpressed with a fold change greater than 2. These three molecules are known to contribute to the clonal expansion, survival, and development of T cells and regulate CD28 co-stimulation to promote Th1 cell responses. Consequently, this HDACi improves the immune response against the cancer cells.

The invention claimed is:

1. A method for treating a subject suffering from a cancer, comprising administrating simultaneously, separately, or sequentially to the subject a therapeutically effective amount of:

(i) an agent that induces MHC-I presentation of antigens, wherein the agent is a histone deacetylase inhibitor (HDACi);

(ii) a vaccine composition comprising inactivated pluripotent or fetal stem cells, as an immunogenic element; and (iii) an adjuvant, wherein the adjuvant is an agonist of toll-like receptor (TLR) 3.

2. The method of claim 1, wherein the vaccine composition comprises inactivated fetal stem cells containing a multiplicity of fetal antigens.

3. The method of claim 1, wherein the pluripotent or fetal stem cells express one or more antigens also expressed by the cancer cells of the subject.

4. The method of claim 2, wherein the inactivated fetal stem cells are obtained by a process comprising:

(a) differentiating a population of pluripotent cells along a pathway specific to the subject's cancer;

(b) expanding the differentiated cells, while optionally exposing the differentiated cells to a mutagenic agent to induce mutagenesis;

(c) verifying that at least 70% of the expanded cells express fetal markers;

(d) optionally, verifying that the expanded cells express at least one tumor associated antigen (TAA) or neo-antigen that is present in the subject's cancer cells; and (e) inactivating the expanded cells to eliminate their ability to divide.

5. The method of claim 1, wherein the pluripotent stem cells are obtained by a process comprising:

(a) expanding pluripotent cells under conditions that maintain their pluripotency, optionally in the presence of an agent that induces MHC-I presentation of antigens during the expansion; and (b) exposing the expanded cells to an inactivating agent to inactivate the expanded pluripotent cells while maintaining cell envelope integrity.

6. The method of claim 1, wherein the histone deacetylase inhibitor is selected from Valproic acid (VPA), Vorinostat, Panobinostat, Givinostat, Belinostat, Levetiracetam, Entinostat, Mocetinostat, Practinostat, Chidamide, Quisinostat, and Abexinostat.

7. The method of claim 1, wherein the TLR3 agonist is Poly(A:U) or poly(I:C).

8. The method of claim 1, wherein the vaccine composition containing the immunogenic element and the agonist of TLR 3 is initially administered followed by multiple administrations of the histone deacetylase inhibitor.

9. The method of claim 1, wherein the cancer is selected from liver cancer, bladder carcinoma, breast carcinoma, cervical carcinoma, cholangiocarcinoma, colorectal carcinoma, gastric sarcoma, glioma, glioblastoma, lung carcinoma, lymphoma, acute lymphoid leukemia, chronic lymphoid leukemia, myeloid leukemias, melanoma, multiple myeloma, osteosarcoma, ovarian carcinoma, pancreatic carcinoma, prostate carcinoma, stomach carcinoma, renal carcinoma, head and neck tumor, hematopoietic malignancies, and RET-mutated endocrine tumors.

10. The method of claim 1, wherein the cancer is a hormone-dependent cancer.

11. The method of claim 10, wherein the cancer is selected from a breast cancer, a prostate cancer, a uterus cancer, and an ovary cancer.

12. The method of claim 9, wherein the RET-mutated endocrine tumor is a medullary thyroid cancer.

13. The method of claim 4, wherein the pluripotent cells are exposed to the mutagenic agent during expansion.

14. The method of claim 5, wherein the pluripotent cells are exposed to the mutagenic agent during expansion.

15. The method of claim 13, wherein the mutagenic agent is N-ethyl-N-nitrosourea (ENU).

16. The method of claim 14, wherein the mutagenic agent is N-ethyl-N-nitrosourea (ENU).

* * * * *